(12) United States Patent
Jain et al.

(10) Patent No.: US 12,080,389 B2
(45) Date of Patent: Sep. 3, 2024

(54) SCALABLE DYNAMIC DATA TRANSMISSION

(71) Applicant: UnitedHealth Group Incorporated, Minnetonka, MN (US)

(72) Inventors: Manoj K. Jain, Bridgewater, NJ (US); Udai K. Raju, South Windsor, CT (US); Sofia Farzan Fayazdeen, Clinton, NJ (US); Julius Cardozo, Ashburn, VA (US); Meredith A. Hardiman, Annandale, NJ (US); Sandesh Jajoo, Bridgewater, NJ (US); Diana Lisi, Stratford, CT (US); Jacqueline H. Goldfinger, West Windsor, NJ (US)

(73) Assignee: UnitedHealth Group Incorporated, Minnetonka, MN (US)

( * ) Notice: Subject to any disclaimer, the term of this patent is extended or adjusted under 35 U.S.C. 154(b) by 632 days.

(21) Appl. No.: 17/162,627

(22) Filed: Jan. 29, 2021

(65) Prior Publication Data
US 2022/0245086 A1    Aug. 4, 2022

(51) Int. Cl.
*H04L 69/06* (2022.01)
*G16H 10/60* (2018.01)
*G16H 15/00* (2018.01)

(52) U.S. Cl.
CPC ............ *G16H 10/60* (2018.01); *G16H 15/00* (2018.01); *H04L 69/06* (2013.01)

(58) Field of Classification Search
CPC ......... G16H 10/60; G16H 15/00; H04L 69/06
See application file for complete search history.

(56) References Cited

U.S. PATENT DOCUMENTS

| | | |
|---|---|---|
| 6,330,243 B1 | 12/2001 | Strandberg |
| 7,281,211 B2 | 10/2007 | Jeannette et al. |
| 7,650,353 B2 | 1/2010 | Machiraju et al. |
| 7,725,818 B1 | 5/2010 | Krishnan et al. |
| 8,296,461 B2 | 10/2012 | Sirdevan et al. |
| 9,946,694 B2 | 4/2018 | Mai et al. |

(Continued)

FOREIGN PATENT DOCUMENTS

JP        5467745 B2    4/2014

OTHER PUBLICATIONS

Lee, Ronald M. et al. "Soft-Coded Trade Procedures for Open-EDI," International Journal of Electronic Commerce, vol. 1, No. 1, Sep. 1996, (14 pages). DOI: 10.1080/10864415.1996.11518275.

(Continued)

*Primary Examiner* — Jonathan Ng
*Assistant Examiner* — Benjamin L. Hanks
(74) *Attorney, Agent, or Firm* — Alston & Bird LLP

(57) ABSTRACT

In general, embodiments of the present invention provide methods, apparatus, systems, computing devices, computing entities, and/or the like for performing scalable dynamic data transmissions. Certain embodiments of the present invention utilize systems, methods, and computer program products that perform scalable dynamic data transmission using structured data responses that include structured response extensions, where the structured response extensions may include dynamic extension response fields generated based on a structured request header of a corresponding structured data request.

19 Claims, 10 Drawing Sheets

(56) References Cited

U.S. PATENT DOCUMENTS

| | | |
|---|---|---|
| 10,062,115 B2 | 8/2018 | Taylor et al. |
| 10,498,858 B2 | 12/2019 | Morton et al. |
| 10,585,979 B2 | 3/2020 | Moyers |
| 2007/0143792 A1 | 6/2007 | Acton et al. |
| 2007/0168301 A1* | 7/2007 | Eisner ................ H04L 49/3009 |
| | | 705/79 |
| 2008/0126386 A1 | 5/2008 | Gaurav et al. |
| 2010/0083084 A1* | 4/2010 | Cicman ................ G06Q 10/10 |
| | | 715/234 |
| 2016/0342751 A1* | 11/2016 | Alstad .................... G16H 40/20 |
| 2016/0371522 A1 | 12/2016 | Snyder et al. |

OTHER PUBLICATIONS

Michopoulos, John et al. "FemML For Data Exchange Between FEA Codes," CMS Group, Naval Research Laboratory, ANSYS Users' Group Conference, Oct. 2, 2001, pp. 1-26, University of Maryland, College Park, MD.

United Healthcare. "Standard Companion Guide—Refers To The Implementation Guide Based On X12 Version 005010X212," Companion Guide Version No. 4.0, Nov. 1, 2020, pp. 1-19. [Available online] <URL: https://www.uhcprovider.com/content/dam/provider/docs/public/resources/edi/EDI-276-277-Companion-Guide-005010X212.pdf>.

* cited by examiner

Sample API Request 500

```
"header": {                                          501
    "businessPartnerId": "BS321GRACEZI",                  511
},
"typeOfRequest": "276",                              512
"msgPayload": "ISA*00" "00" "ZZ*BS321GRACEZI" "ZZ*UNITEDHEALTH..."  513
                502
"requestExtensions": {                               503
    "extensions": [
        {
            "type": "CLAIM_STATUS"
        },
        {
            "type": "COB"
        }
    ]
}
```

Allowed values for "type":
- "CLAIM_STATUS"
- "CHECK"
- "COB"
- Combination of any of them
- In future, more extensions be added

FIG. 5

Sample API Response

```
{
"header": { 801
"businessPartnerId": "BS321GRACEZI", 811
...
"typeOfResponse": "277" 812
},
"responsePayload":
"ISA*00*         *00*         *ZZ*BS321GRACEZI *190423*0740*^*00501*123265178*0*P*~...",
                                                            813
"responseExtension": { 803
"extensions": [
{"resourceType": "ClaimResponse", ..."id": "x999", "text": { "status": "generated", "div": "<div 
xmlns='http://www.w3.org/1999/xhtml'>A human-readable rendering of the ClaimResponse</div>"
},
{"category": {
"coding": [{
"code": "eligible" }] },
"amount": {
"value": 135.57,
"currency": "USD" } },
{"category": {
"coding": [{
"code": "copay" }] },
"amount": {
"value": 10.00,
"currency": "USD" } }, ]
}
]
}
}
```

- Gives Providers access to critical data for operational needs
- Reduces Phone Calls
- Leverage existing services for X12 with little change to consume additional data
- Flexible integration with any consumer system

FIG. 8

```
{
  "type": "PRIOR_AUTH",
  "params": [
    {
      "name": "procedureCode",
      "value": "43860"
    },                              901
    {
      "name": "diagnosisCode",
      "value": "Z68.32"
    },                              902
  ]
}
```

```
{
"parameters": {
"businessPartnerId": "",
"businessPartnerReferenceNumber": "nexAPI1",
"returnCode": "000",
"returnCodeDescription": "Success",
"trackingId": "039-1588969332941-1661992220",
"transactionVersion": "1.0",
"typeOfRequest": "276",
"typeOfResponse": "277"
},
"message": " ISA*00* *00* *33*87726 *ZZ*BS321GRACEZI
*200508*1522*^*00501*169335353*0*P*:~GS*HN*061118515*B00099999800*20200508*1522*1*
X*005010X212~ST*277*000000001*005010X212~BHT*0010*08*189708849*20200508*15221537*D
G~HL*1**20*1~
NM1*PR*2*UNITEDHEALTHCARE*****PI*87726~HL*2*1*21*1~NM1*41*2*****46*222222221~HL
*3*2*19*1~NM1*1P*2******XX*1666666666~HL*4*3*22*0~NM1*IL*1*NAME*FIRST****MI*00000
0000~TRN*2*CSBCID62726896~
STC*F1:104*20200122**372*84.17*20200114**20200122*C0000006~REF*1K*9918046987~REF*BLT
*343~REF*EJ*897327846920~DTP*472*D8*20200102~SVC*HC:T1030*372*84.17*0551***1~STC*F1:
104*20200122~REF*FJ*3877537099Z1~DTP*472*D8*20200102~
SE*21*000000001~GE*1*1~IEA*1*169335353~",
```

FIG. 10

SCALABLE DYNAMIC DATA TRANSMISSION

BACKGROUND

Various embodiments of the present invention address technical challenges related to performing dynamic data transmission in complex data transmission environments and address various efficiency and reliability shortcomings of existing dynamic data transmission solutions.

BRIEF SUMMARY

In general, embodiments of the present invention provide methods, apparatus, systems, computing devices, computing entities, and/or the like for performing scalable dynamic data transmissions. Certain embodiments of the present invention utilize systems, methods, and computer program products that perform scalable dynamic data transmission using structured data responses that include structured response extensions, where the structured response extensions may include dynamic extension response fields generated based on a structured request header of a corresponding structured data request.

In accordance with one aspect, a method is provided. In one embodiment, the method comprises: identifying a structured data request, wherein: (i) the structured data request comprises a structured request header, a structured request payload, and a structured request extension, (ii) the structured request header describes a requester identifier, and (iii) the structured request payload describes a predefined transactional inquiry; determine, based on the predefined transactional inquiry, a predefined transactional response associated with the structured data request; determining, based on the structured request extension and the request identifier, one or more extension response fields associated with the structured data request, wherein: (i) the one or more extension response fields comprise one or more dynamic extension response fields, and (ii) the one or more dynamic extension response fields are determined based on the request identifier; generating a structured data response for the structured data request, wherein: (i) the structured data response comprises a structured response payload and a structured response extension, (ii) the structured response payload describes the predefined transactional response, and (ii) the structured response extension describes the one or more extension response fields; and causing the structured data response to be transmitted to a client computing entity, wherein the client computing entity is configured to perform one or more response-based actions based on the structured data response.

In accordance with another aspect, a computer program product is provided. The computer program product may comprise at least one computer-readable storage medium having computer-readable program code portions stored therein, the computer-readable program code portions comprising executable portions configured to: identify a structured data request, wherein: (i) the structured data request comprises a structured request header, a structured request payload, and a structured request extension, (ii) the structured request header describes a requester identifier, and (iii) the structured request payload describes a predefined transactional inquiry; determine, based on the predefined transactional inquiry, a predefined transactional response associated with the structured data request; determine, based on the structured request extension and the request identifier, one or more extension response fields associated with the structured data request, wherein: (i) the one or more extension response fields comprise one or more dynamic extension response fields, and (ii) the one or more dynamic extension response fields are determined based on the request identifier; generate a structured data response for the structured data request, wherein: (i) the structured data response comprises a structured response payload and a structured response extension, (ii) the structured response payload describes the predefined transactional response, and (ii) the structured response extension describes the one or more extension response fields; and cause the structured data response to be transmitted to a client computing entity, wherein the client computing entity is configured to perform one or more response-based actions based on the structured data response.

In accordance with yet another aspect, an apparatus comprising at least one processor and at least one memory including computer program code is provided. In one embodiment, the at least one memory and the computer program code may be configured to, with the processor, cause the apparatus to: identify a structured data request, wherein: (i) the structured data request comprises a structured request header, a structured request payload, and a structured request extension, (ii) the structured request header describes a requester identifier, and (iii) the structured request payload describes a predefined transactional inquiry; determine, based on the predefined transactional inquiry, a predefined transactional response associated with the structured data request; determine, based on the structured request extension and the request identifier, one or more extension response fields associated with the structured data request, wherein: (i) the one or more extension response fields comprise one or more dynamic extension response fields, and (ii) the one or more dynamic extension response fields are determined based on the request identifier; generate a structured data response for the structured data request, wherein: (i) the structured data response comprises a structured response payload and a structured response extension, (ii) the structured response payload describes the predefined transactional response, and (ii) the structured response extension describes the one or more extension response fields; and cause the structured data response to be transmitted to a client computing entity, wherein the client computing entity is configured to perform one or more response-based actions based on the structured data response.

BRIEF DESCRIPTION OF THE DRAWINGS

Figure 1:
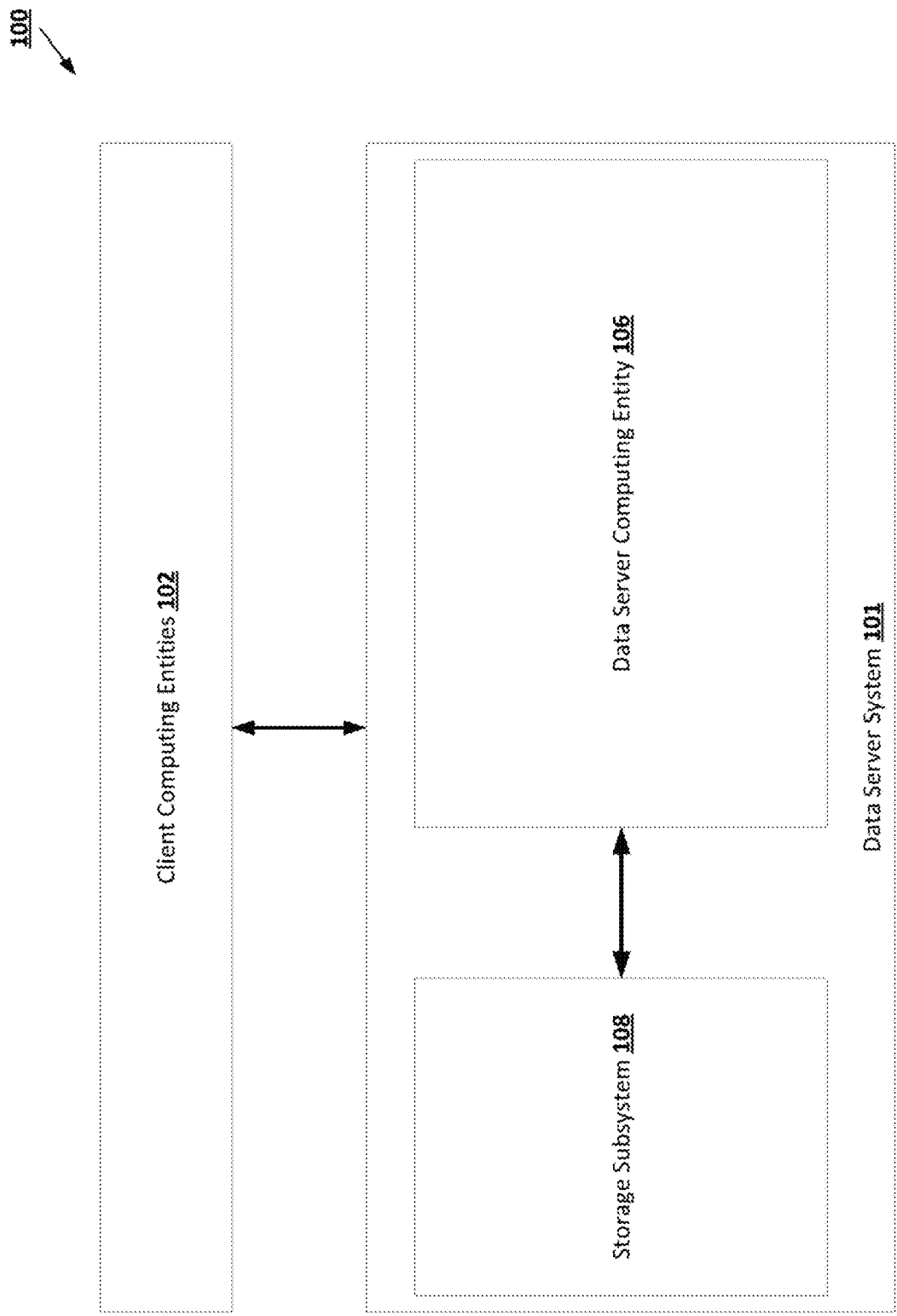

Having thus described the invention in general terms, reference will now be made to the accompanying drawings, which are not necessarily drawn to scale, and wherein:

FIG. 1 provides an exemplary overview of an architecture that can be used to practice embodiments of the present invention.

Figure 2:
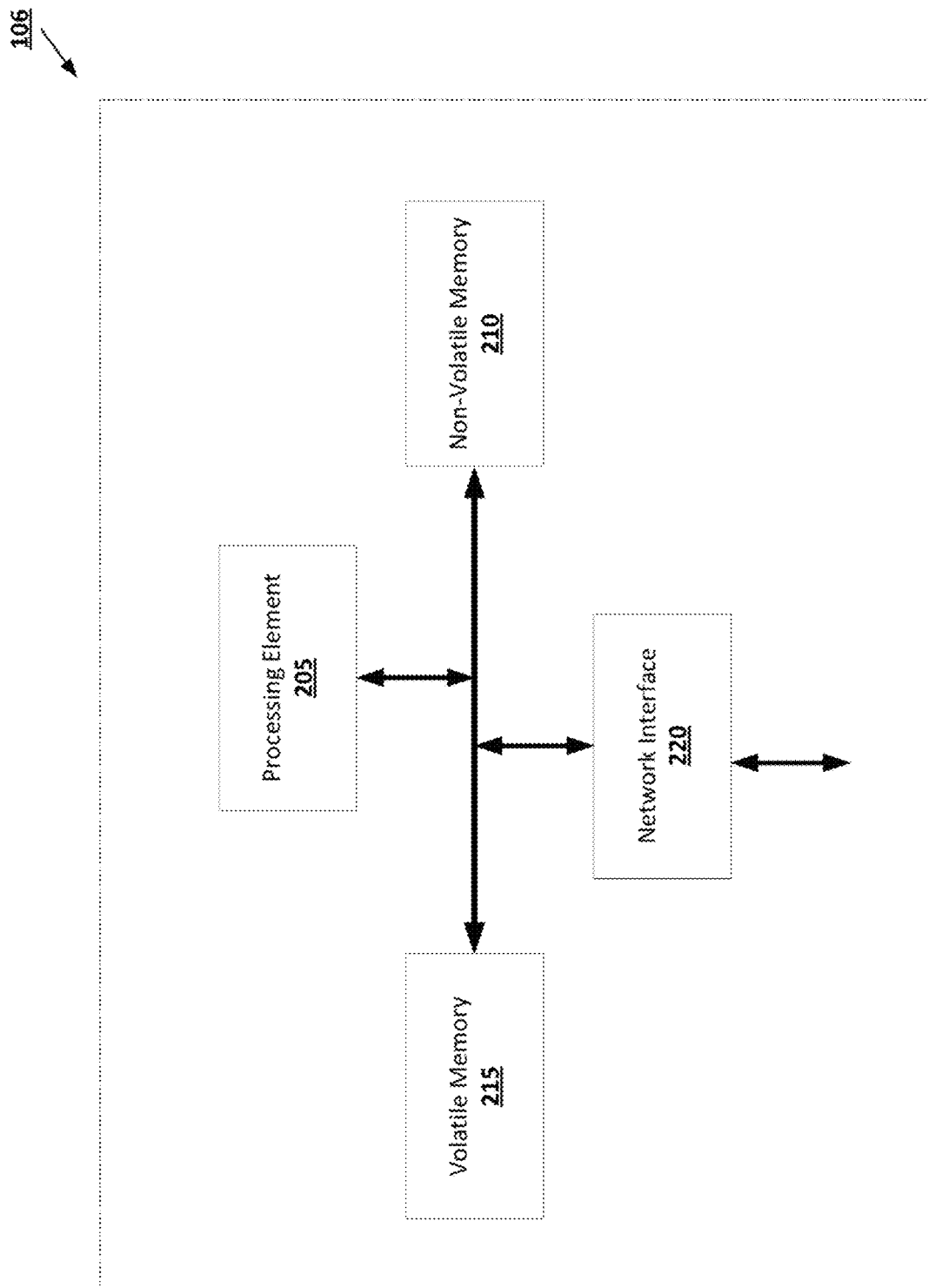

FIG. 2 provides an example data server computing entity in accordance with some embodiments discussed herein.

Figure 3:
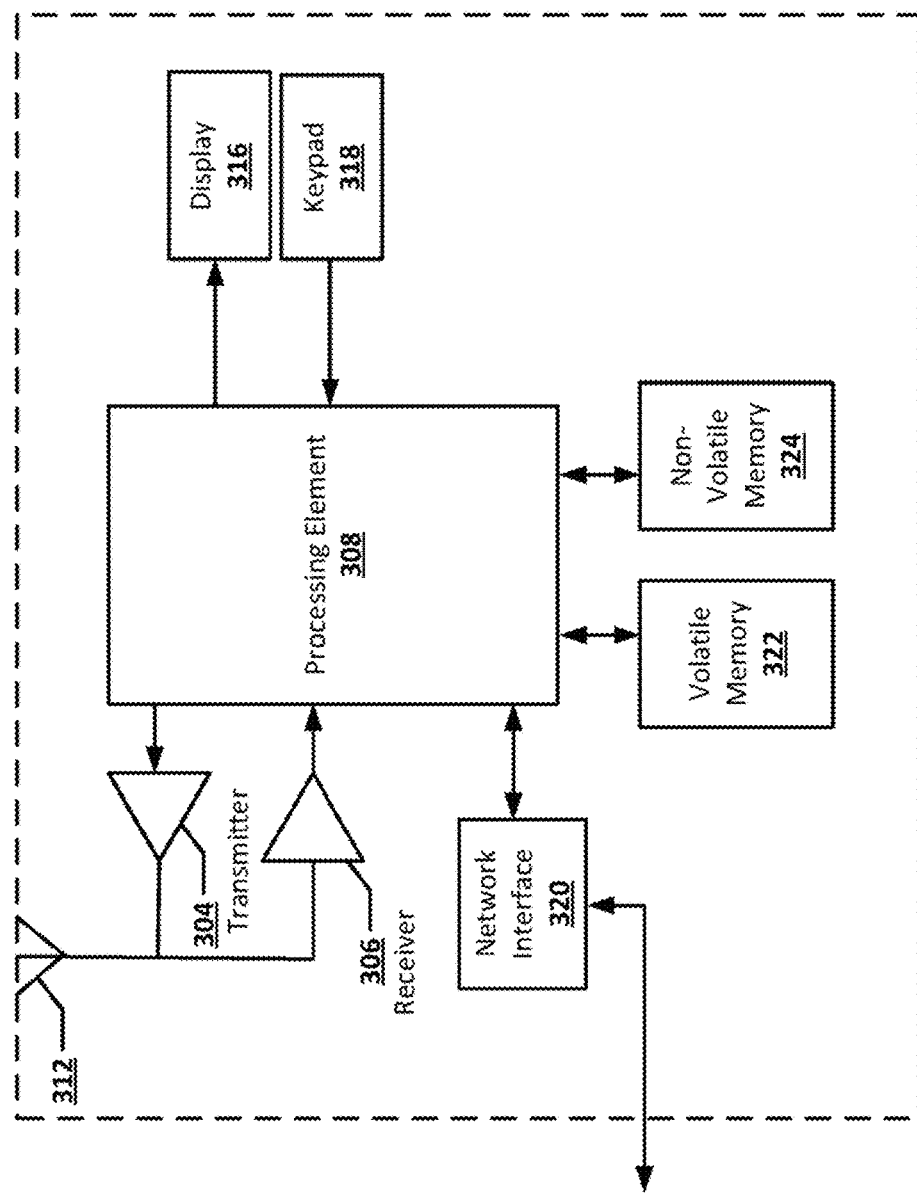

FIG. 3 provides an example client computing entity in accordance with some embodiments discussed herein.

Figure 4:
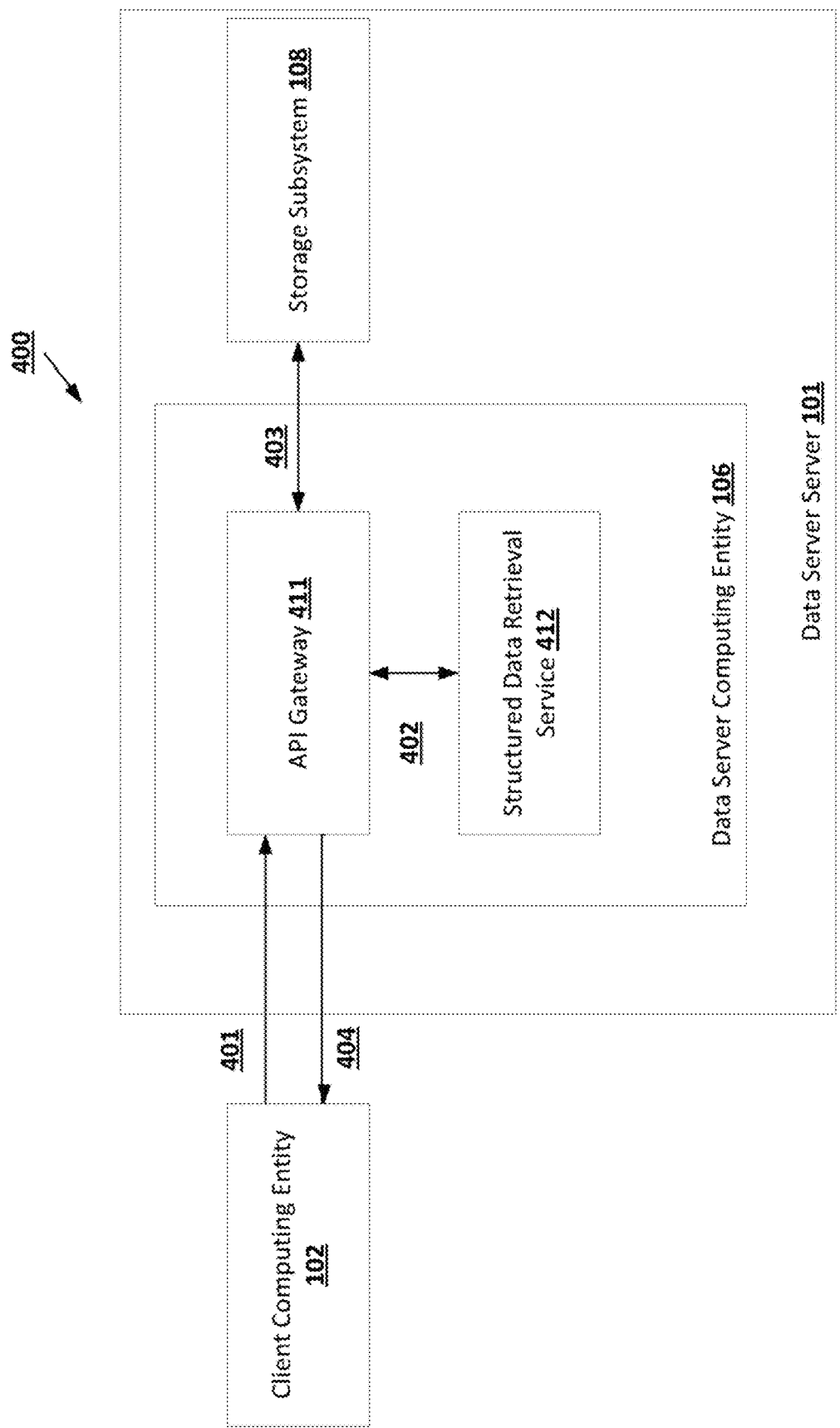

FIG. 4 is a transmission flow diagram of an example process for performing scalable dynamic data transmission in accordance with some embodiments discussed herein.

FIG. 5 provides an operational example of a structured data request in accordance with some embodiments discussed herein.

Figure 6:
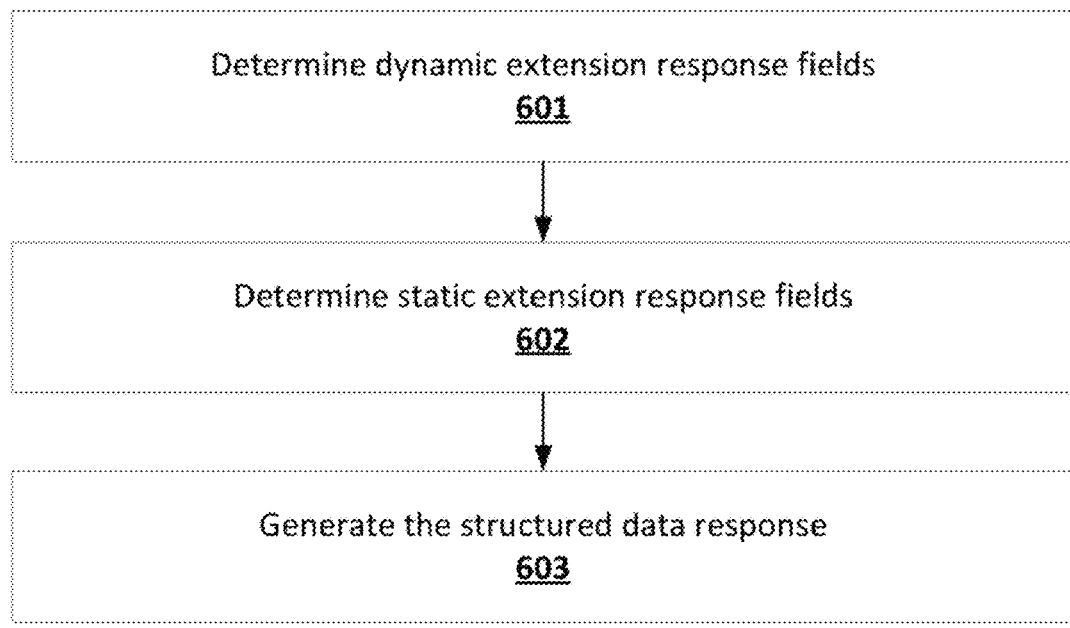

FIG. 6 is a flowchart diagram of an example process for generating a structured data response in accordance with some embodiments discussed herein.

Figure 7:
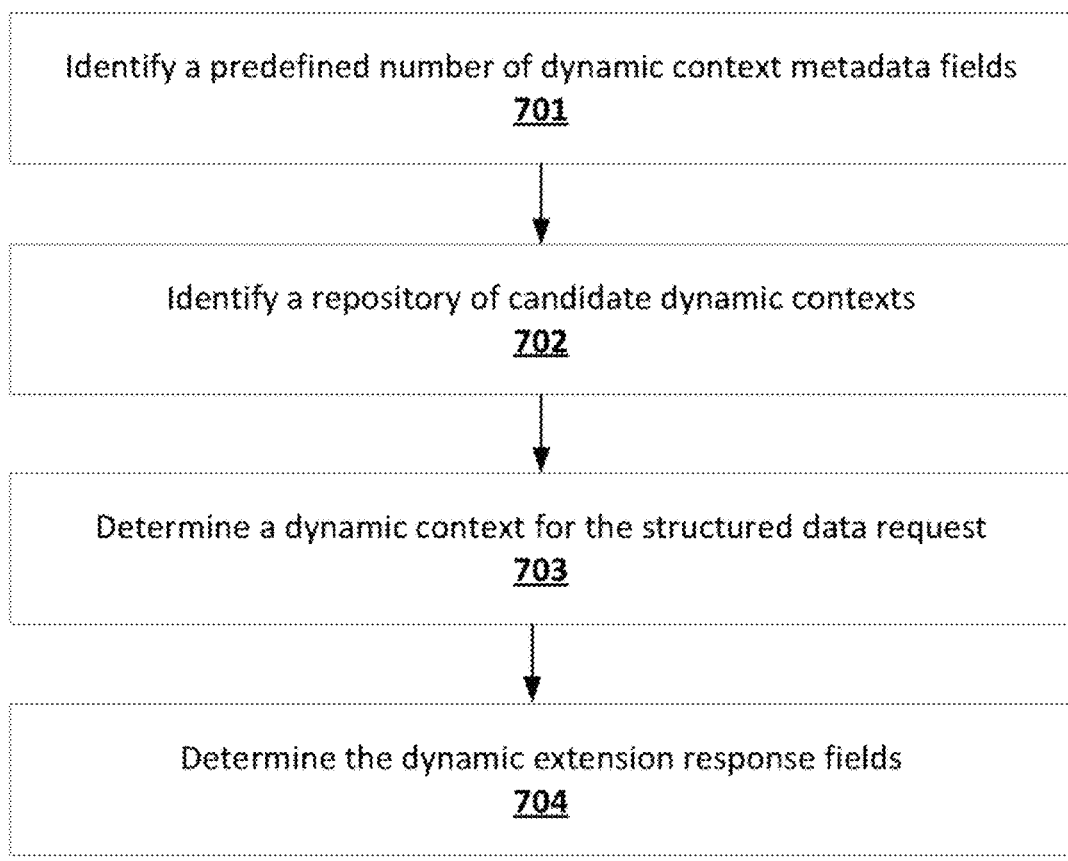

FIG. 7 is a flowchart diagram of an example process for determining dynamic response extension fields in accordance with some embodiments discussed herein.

FIG. 8 provides an operational example of a structured data response in accordance with some embodiments discussed herein.

FIG. 9 provides an operational example of a structured response extension for a structured data response in accordance with some embodiments discussed herein.

FIG. 10 provides an operational example of a structured data response in accordance with some embodiments discussed herein.

DETAILED DESCRIPTION

Various embodiments of the present invention now will be described more fully hereinafter with reference to the accompanying drawings, in which some, but not all, embodiments of the inventions are shown. Indeed, these inventions may be embodied in many different forms and should not be construed as limited to the embodiments set forth herein; rather, these embodiments are provided so that this disclosure will satisfy applicable legal requirements. The term "or" is used herein in both the alternative and conjunctive sense, unless otherwise indicated. The terms "illustrative" and "exemplary" are used to be examples with no indication of quality level. Like numbers refer to like elements throughout. Moreover, while certain embodiments of the present invention are described with reference to predictive data analysis, one of ordinary skill in the art will recognize that the disclosed concepts can be used to perform other types of data analysis.

I. OVERVIEW AND TECHNICAL IMPROVEMENTS

Various embodiments of the present invention address technical challenges related to efficiency and reliability of performing scalable dynamic data transmission in complex data transmission environments. Complex data transmission environments are often characterized by a large number of data requester profiles, a large number of data request types, and/or a large number of data request conditions. Because dynamic data transmission often requires taking into account the data requester profiles, the data request types, and/or data request conditions when generating data request responses, the complexity of the noted data transmission environments presents significant challenges for efficiently and reliably generating data request responses under reasonable time constraints. This challenge is compounded as the number of data requester profiles, the data request types, and/or data request conditions increases. In some embodiments, the increase in the number of data requester profiles, the data request types, and/or data request conditions requires storing large amounts of configuration data often in a distributed manner, a feature that further undermines the efficiency and reliability of performing scalable dynamic data transmission in complex data transmission environments.

To address the above-noted challenges associated with efficiency and reliability of performing scalable dynamic data transmission in complex data transmission environments, various embodiments of the present invention enable generating structured data responses that separately describe standardized portions of the response from "customized" portions of the response, thus enabling generating the former segment in a conventional fashion while utilizing dynamic processing only for generating the latter segment. Accordingly, in some embodiments, the structured data retrieval service may be configured to have a static logic that is configured to process structured data requests in a uniform manner irrespective of general properties of structured data requests as specified by structured requester headers and/or irrespective of extension requests described by structured data extensions. This in turn enables a data server computing entity to limit the portions of the data exchange logic of the data server computing entity that need to be modified to enable dynamic data exchange in a scalable fashion.

By utilizing the above-noted techniques, various embodiments of the present invention are configured to limit the need for dynamic data generation, which in turn makes it less resource-intensive to make dynamic data generation frameworks scalable. In this way, various embodiments of the present invention reduce the number of computational resources and/or storage resources needed to perform dynamic data transmission, and makes significant technical contributions to improving the scalability of dynamic data transmission systems.

Moreover, various embodiments of the present invention are configured to provide, to client computing entities, dynamically-generated structured data responses that are likely to describe a more comprehensive set of data fields relative to non-dynamically-generated structured data responses. Because of their greater levels of comprehensiveness resulting from their more intelligent generation, providing dynamically-generated structured data responses is likely to reduce the overall number of structured data requests that are transmitted by client computing entities to data server computing entities, as the client computing entities are likely to receive their target information fields in a fewer number of structured data responses and via a fewer number of structured data requests. This in turn both reduces the operational cost of maintaining data server computing entities and reduces network transmissions across client-server networks connecting data server computing entities and client computing entities by reducing the number of network calls from client computing entities to data server computing entities across the noted client-server networks. Accordingly, by providing dynamically-generated structured data responses to client computing entities, various embodiments of the present invention improve both operational efficiency of data server computing entities and network efficiency of client-server networks connecting data server computing entities and client computing entities.

II. DEFINITIONS

The term "structured data request" may refer to a data entity that is configured to describe data fields of a request by a client computing entity to obtain a structured data response that comprises a predefined transactional response, along with optionally one or more other data fields. The structured data request may include: (i) a structured request header that describes one or more general metadata fields associated with the structured data request, such as at least one of a requester identifier (e.g., an identifier of the trading partner) associated with the structured data request, a request type identifier (e.g., a request type identifier describing that the structured data request is an electronic data interchange (EDI) 276 claim status request), a request time identifier (e.g., a request time identifier describing a generation time of the structured data request, a request time identifier describing a transmission time of the structured data request by a client computing entity, a request time identifier describing a receipt time of the structured data request by a data server computing entity, and/or the like); (ii) a structured request payload that describes a predefined transactional inquiry (e.g., a standardized transactional request, such as an EDI request including an EDI 276 claim status request) associated with the structured data request; and (iii) a structured request extension that may describe one or more extension request fields associated with the structured response field. In some embodiments, the predefined transactional inquiry specified by the structured request payload of the structured data request may be used to generate the predefined transactional response in the structured data response that is generated in response to the structured data request. In some embodiments, at least one of the one or more general metadata fields associated with the structured data request described by the structured request header or the one or more extension request fields described by the structured request extension may be used to generate a structured response extension of the structured data response that is generated in response to the structured data request. In some embodiments, the structured data request is a JavaScript Object Notation (JSON) file.

The term "structured request payload" may refer to a data entity that is configured to describe a segment (e.g., a continuous segment, such as a defined payload data field) of a structured data request that describes a predefined transactional inquiry associated with the structured data request, where the predefined transactional inquiry is a transactional inquiry that is formatted in accordance with a transactional inquiry/response formatting scheme such as a standardized transactional inquiry/response formatting scheme. An example of a standardized transactional inquiry/response formatting scheme is an EDI transactional inquiry/response formatting scheme, and examples of predefined transactional inquiries that may be generated using the EDI transactional inquiry/response formatting scheme include an EDI 276 predefined transactional inquiry, aspects of which are described in United Healthcare, Standard Companion Guide (Companion Guide Version Number 4.0, published Nov. 1, 2020), available online at https://www.uhcprovider.com/content/dam/provider/docs/public/resources/edi/EDI-276-277-Companion-Guide-005010X212.pdf. In some embodiments, the predefined transactional inquiry is an EDI inquiry. In some of the noted embodiments, the EDI inquiry is an EDI 276 inquiry. In some embodiments, an identifier (e.g., a numeric identifier) of a request type of the predefined transactional inquiry (e.g., as defined by the corresponding transactional inquiry/response formatting scheme and/or as defined by a data server computing entity) is provided as part of the general metadata fields described by the structured request header of the structured data request to which the structured request payload belongs (e.g., as the request type identifier of the structured request header of the structured data request to which the structured request payload belongs). While various embodiments of the present invention are described with reference to an exemplary embodiment in which a structured data request describes one predefined transactional inquiry only, a person of ordinary skill in the relevant technology will recognize that a structured request payload may in some embodiments describe two or more predefined transactional inquiries without departing from the spirit of the present invention.

The term "structured request extension" may refer to a data entity (e.g., an optional data entity) that is configured to describe a segment (e.g., a continuous segment) of a structured data request that may optionally describe one or more extension request fields associated with the structured data request. The structured request extension may enable a client computing entity to explicitly request data beyond the data provided in response to a predefined transactional inquiry described by the structured request payload of the structured data request. Importantly, however, the structured request extension may in some embodiments describe no extension requests fields (i.e., "is empty"), in order to enable the client computing entity to make requests for predefined transactional responses via predefined transactional inquiries without explicitly specifying extension request fields. In some embodiments, even when the structured request extension of a structured data response is empty such that no extension requests fields are specified by the structured request extension, a structured response extension of a structured data response generated in response to the structured data response may include extension response fields (e.g., may be "non-empty"). This may be because, in at least some embodiments, the extension response fields described by a structured response extension of a structured data response may include static extension response fields determined based on the one or more extension request fields described by a structured request extension of a corresponding structured data request as well as dynamic extension response fields determined based on a subset of the general metadata fields described by the structured request header of the corresponding structured data request. In some embodiments, when a structured data request (e.g., the structured request payload of the structured data request) relates to two or more claim data entities (e.g., relates to two or more health insurance claims), the structured response extension of the structured data response corresponding to the structured data request describes/designates, for each of the two more claim data entities, a set of fields of the structured response extension that relate to the claim data entity.

The term "structured data response" may refer to a data entity that is configured to describe one or more data fields of a response by a data server computing entity to a structured data request by a client computing entity, where the one or more data fields comprise a predefined transactional response to a predefined transactional inquiry described by the structured data request, along with one or more optional other fields. The structured data response may include: (i) a structured response header that describes one or more general metadata fields associated with the structured data response and/or the corresponding structured data request, such as at least one of a requester identifier (e.g., an identifier of the trading partner) associated with the structured data request, a response type identifier (e.g., a response type identifier describing that the structured data response is an EDI 277 claim status response), a response time identifier (e.g., a response time identifier describing a generation time of the structured data response, a response time identifier describing a transmission time of the structured data response by a data server computing entity, and/or the like); (ii) a structured response payload that describes a predefined transactional response (e.g., a standardized transactional response, such as an EDI response including an EDI 277 claim status response) associated with the structured data response; and (iii) a structured response extension that may describe one or more extension response fields associated with the structured response field. In some embodiments, the predefined transactional response specified by the structured response payload of the structured data response may be generated based on the predefined transactional inquiry in the corresponding structured data request. In some embodiments, the structured data response is a JavaScript Object Notation (JSON) file.

The term "structured response header" may refer to a data entity that is configured to describe a segment (e.g., a continuous segment) of a structured data response that describes one or more general metadata fields associated with the structured data response and/or the corresponding structured data request, wherein all valid structured data responses generated by the data server computing entity may be required by the data server computing entity to describe acceptable values for all of the one or more "general" metadata fields. As such, the one or more general metadata fields described by the structured response header may correspond to properties of structured data requests and/or structured data responses that apply to different structured data requests and/or different structured data responses having different structured data request types and/or having different structured data response types and being associated with different structured data requester profiles. Examples of such properties include: (i) a requester identifier that describes a structured requester profile associated with a corresponding structured data request (e.g., a requester identifier that describes an identifier of the trading partner associated with the structured data request), (ii) a response type identifier that describes a structured data response type associated with a structured data response (e.g., a response type identifier that describes that a structured data response is an EDI 277 claim status response), and (iii) a response time identifier that describes a structured data response time associated with the structured data response (e.g., a response time identifier that describes a generation time of the structured data response, a request time identifier that describes a particular transmission time of the structured data response, and/or the like).

The term "structured request payload" may refer to a data entity that is configured to describe a segment (e.g., a continuous segment) of a structured data response that describes a predefined transactional response associated with the structured data response, where the predefined transactional response is a transactional response that is formatted in accordance with a transactional inquiry/response formatting scheme such as a standardized transactional inquiry/response formatting scheme. An example of a standardized transactional inquiry/response formatting scheme is an EDI transactional inquiry/response formatting scheme, and examples of predefined transactional responses that may be generated using the EDI transactional inquiry/response formatting scheme include an EDI 277 predefined transactional response, aspects of which are described in United Healthcare, Standard Companion Guide (Companion Guide Version Number 4.0, published Nov. 1, 2020), available online at https://www.uhcprovider.com/content/dam/provider/docs/public/resources/edi/EDI-276-277-Companion-Guide-005010X212.pdf. In some embodiments, the predefined transactional response is an EDI response. In some of the noted embodiments, the EDI response is an EDI 277 claim status response. In some embodiments, an identifier (e.g., a numeric identifier) of a response type of the predefined transactional response (e.g., as defined by the corresponding transactional inquiry/response formatting scheme and/or as defined by a data server computing entity) is provided as part of general metadata fields described by a structured response payload of the structured data response to which the structured response payload belongs (e.g., as the response type identifier of the structured response header of the structured data response to which the structured response payload belongs). While various embodiments of the present invention are described with reference to an exemplary embodiment in which a structured data request describes one predefined transactional inquiry only, a person of ordinary skill in the relevant technology will recognize that a structured request payload may in some embodiments describe two or more predefined transactional inquiries without departing from the spirit of the present invention. In some of those embodiments, when the structured request payload of a structured data request describes two or more predefined transactional inquiries, the structured response payload of a structured data response that is generated in response to the structured data request describes two or more predefined transactional responses (e.g., a predefined transactional response corresponding to each of the two or more predefined transactional inquiries).

The term "structured response extension" may refer to a data entity that is configured to describe a segment (e.g., a continuous segment) of a structured data response that describes one or more extension response fields of the noted structured data response. In some embodiments, the extension response fields described by a structured response extension of a structured data response may include at least one of static extension response fields determined based on the one or more extension request fields described by a structured request extension of a corresponding structured data request or dynamic extension response fields determined based on a subset of the general metadata fields described by the structured request header of the corresponding structured data request. In some embodiments, the structured request extension may enable a client computing entity to explicitly request data beyond the data provided in response to a predefined transactional inquiry described by the structured request payload of the structured data request. In some of the noted embodiments, these data requests (aka. "request extension data fields) are used to determine static extension response fields of the structured response extension.

The term "dynamic extension response field" may refer to a data entity that is configured to describe a data field included in a structured data response based on a general metadata property of a corresponding structured data request as described by a structured request header of the structured data request. In some embodiments, to generate the dynamic extension response fields in response to a structured data request, a data server computing entity: (i) identifies a predefined number of dynamic context metadata fields of the structured request header of the structured data request as defined by configuration data of the data server computing entity, (ii) queries a repository of dynamic contexts based on the dynamic context metadata fields to determine a dynamic context of the structured data request, and (iii) determines the dynamic extension response fields based on a set of dynamic response extension fields associated with the dynamic context.

The term "dynamic context metadata field" may refer to a data entity that is configured to describe a metadata field described by a structured request header of the structured data request that may be used to infer dynamic response extension fields for a corresponding structured data response. For example, in an embodiment in which different sets of dynamic extension response fields are defined for different requester identifiers, the predefined number of dynamic context metadata fields may include the requester identifier field. As another example, in an embodiment in which different sets of dynamic extension response fields are defined for different request type identifiers, the predefined number of dynamic context metadata fields may include the request type identifier field. As a further example, in an embodiment in which different sets of dynamic extension response fields are defined for different request time identifiers, the predefined number of dynamic context metadata fields may include the request time identifier field. As a further example, in an embodiment in which different sets of dynamic extension response fields are defined for different requester identifiers and/or different request type identifiers, the predefined number of dynamic context metadata fields may include the requester identifier field and the request type identifier field. As an additional example, in an embodiment in which different sets of dynamic extension response fields are defined for different requester identifiers, different request type identifiers, and/or different request time identifiers, the predefined number of dynamic context metadata fields may include the requester identifier field, the request type identifier field, and the request time identifier field.

The term "candidate dynamic context" may refer to a data entity that is configured to describe a combination of the data field values for a subset of the predefined number of dynamic context metadata fields that is assigned to a set of dynamic response extension fields. For example, if the predefined number of dynamic context metadata fields include the requester identifier field, then the dynamic contexts may include: (i) a dynamic context associated with the requester identifier RI1, (ii) a dynamic context associated with the requester identifier RI2, and (iii) a dynamic context associated with the requester identifier RI3. As another example, if the predefined number of dynamic context metadata fields include the requester identifier field, the request type identifier field, and the request time identifier field, then the candidate dynamic contexts may include: (i) a candidate dynamic context associated with the requester identifier RI1, (ii) a candidate dynamic context associated with the requester identifier RI1 and the request type identifier RTPI1, (iii) a candidate dynamic context associated with the requester identifier RI2 and the request time identifier RTMI1, and (iv) a candidate dynamic context associated with the requester identifier RI1, the request type identifier RTPI1, and the request time identifier RTMI2.

The term "static extension response field" may refer to a data entity that is configured to describe a data field included in a structured data response based on a structured request extension field of a structured request extension of a corresponding structured data request. As described above, a structured request extension may describe a contiguous segment of a structured data request that may optionally describe one or more extension request fields associated with the structured data request. The structured request extension may enable a client computing entity to explicitly request data beyond the data provided in response to a predefined transactional inquiry described by the structured request payload of the noted structured data request.

III. COMPUTER PROGRAM PRODUCTS, METHODS, AND COMPUTING ENTITIES

Embodiments of the present invention may be implemented in various ways, including as computer program products that comprise articles of manufacture. Such computer program products may include one or more software components including, for example, software objects, methods, data structures, or the like. A software component may be coded in any of a variety of programming languages. An illustrative programming language may be a lower-level programming language such as an assembly language associated with a particular hardware architecture and/or operating system platform. A software component comprising assembly language instructions may require conversion into executable machine code by an assembler prior to execution by the hardware architecture and/or platform. Another example programming language may be a higher-level programming language that may be portable across multiple architectures. A software component comprising higher-level programming language instructions may require conversion to an intermediate representation by an interpreter or a compiler prior to execution.

Other examples of programming languages include, but are not limited to, a macro language, a shell or command language, a job control language, a script language, a database query or search language, and/or a report writing language. In one or more example embodiments, a software component comprising instructions in one of the foregoing examples of programming languages may be executed directly by an operating system or other software component without having to be first transformed into another form. A software component may be stored as a file or other data storage construct. Software components of a similar type or functionally related may be stored together such as, for example, in a particular directory, folder, or library. Software components may be static (e.g., pre-established or fixed) or dynamic (e.g., created or modified at the time of execution).

A computer program product may include a non-transitory computer-readable storage medium storing applications, programs, program modules, scripts, source code, program code, object code, byte code, compiled code, interpreted code, machine code, executable instructions, and/or the like (also referred to herein as executable instructions, instructions for execution, computer program products, program code, and/or similar terms used herein interchangeably). Such non-transitory computer-readable storage media include all computer-readable media (including volatile and non-volatile media).

In one embodiment, a non-volatile computer-readable storage medium may include a floppy disk, flexible disk, hard disk, solid-state storage (SSS) (e.g., a solid state drive (SSD), solid state card (SSC), solid state module (SSM), enterprise flash drive, magnetic tape, or any other non-transitory magnetic medium, and/or the like. A non-volatile computer-readable storage medium may also include a punch card, paper tape, optical mark sheet (or any other physical medium with patterns of holes or other optically recognizable indicia), compact disc read only memory (CD-ROM), compact disc-rewritable (CD-RW), digital versatile disc (DVD), Blu-ray disc (BD), any other non-transitory optical medium, and/or the like. Such a non-volatile computer-readable storage medium may also include read-only memory (ROM), programmable read-only memory (PROM), erasable programmable read-only memory (EPROM), electrically erasable programmable read-only memory (EEPROM), flash memory (e.g., Serial, NAND, NOR, and/or the like), multimedia memory cards (MMC), secure digital (SD) memory cards, SmartMedia cards, CompactFlash (CF) cards, Memory Sticks, and/or the like. Further, a non-volatile computer-readable storage medium may also include conductive-bridging random access memory (CBRAM), phase-change random access memory (PRAM), ferroelectric random-access memory (FeRAM), non-volatile random-access memory (NVRAM), magnetoresistive random-access memory (MRAM), resistive random-access memory (RRAM), Silicon-Oxide-Nitride-Oxide-Silicon memory (SONOS), floating junction gate random access memory (FJG RAM), Millipede memory, racetrack memory, and/or the like.

In one embodiment, a volatile computer-readable storage medium may include random access memory (RAM), dynamic random access memory (DRAM), static random access memory (SRAM), fast page mode dynamic random access memory (FPM DRAM), extended data-out dynamic random access memory (EDO DRAM), synchronous dynamic random access memory (SDRAM), double data rate synchronous dynamic random access memory (DDR SDRAM), double data rate type two synchronous dynamic random access memory (DDR2 SDRAM), double data rate type three synchronous dynamic random access memory (DDR3 SDRAM), Rambus dynamic random access memory (RDRAM), Twin Transistor RAM (TTRAM), Thyristor RAM (T-RAM), Zero-capacitor (Z-RAM), Rambus in-line memory module (RIMM), dual in-line memory module (DIMM), single in-line memory module (SIMM), video random access memory (VRAM), cache memory (including various levels), flash memory, register memory, and/or the like. It will be appreciated that where embodiments are described to use a computer-readable storage medium, other types of computer-readable storage media may be substituted for or used in addition to the computer-readable storage media described above.

As should be appreciated, various embodiments of the present invention may also be implemented as methods, apparatus, systems, computing devices, computing entities, and/or the like. As such, embodiments of the present invention may take the form of an apparatus, system, computing device, computing entity, and/or the like executing instructions stored on a computer-readable storage medium to perform certain steps or operations. Thus, embodiments of the present invention may also take the form of an entirely hardware embodiment, an entirely computer program product embodiment, and/or an embodiment that comprises combination of computer program products and hardware performing certain steps or operations.

Embodiments of the present invention are described below with reference to block diagrams and flowchart illustrations. Thus, it should be understood that each block of the block diagrams and flowchart illustrations may be implemented in the form of a computer program product, an entirely hardware embodiment, a combination of hardware and computer program products, and/or apparatus, systems, computing devices, computing entities, and/or the like carrying out instructions, operations, steps, and similar words used interchangeably (e.g., the executable instructions, instructions for execution, program code, and/or the like) on a computer-readable storage medium for execution. For example, retrieval, loading, and execution of code may be performed sequentially such that one instruction is retrieved, loaded, and executed at a time. In some exemplary embodiments, retrieval, loading, and/or execution may be performed in parallel such that multiple instructions are retrieved, loaded, and/or executed together. Thus, such embodiments can produce specifically-configured machines performing the steps or operations specified in the block diagrams and flowchart illustrations. Accordingly, the block diagrams and flowchart illustrations support various combinations of embodiments for performing the specified instructions, operations, or steps.

IV. Exemplary System Architecture

FIG. 1 is a schematic diagram of an example architecture 100 for performing scalable dynamic data transmission. The architecture 100 includes a data server system 101 configured to receive data requests from client computing entities 102, process the data requests to generate data responses, and provide the generated data responses to the client computing entities 102. In some embodiments, the data server system 101 may communicate with at least one of the client computing entities 102 using one or more communication networks. Examples of communication networks include any wired or wireless communication network including, for example, a wired or wireless local area network (LAN), personal area network (PAN), metropolitan area network (MAN), wide area network (WAN), or the like, as well as any hardware, software and/or firmware required to implement it (such as, e.g., network routers, and/or the like).

The data server system 101 may include a data server computing entity 106 and a storage subsystem 108. The data server computing entity 106 may be configured to receive data requests from client computing entities 102, process the data requests to generate data responses, and provide the generated data responses to the client computing entities 102. The storage subsystem 108 may be configured to store input data used by the data server computing entity 106 to perform data transmission operations as well as model definition data used by the data server computing entity 106 to perform various data transmission tasks. The storage subsystem 108 may include one or more storage units, such as multiple distributed storage units that are connected through a computer network. Each storage unit in the storage subsystem 108 may store at least one of one or more data assets and/or one or more data about the computed properties of one or more data assets. Moreover, each storage unit in the storage subsystem 108 may include one or more non-volatile storage or memory media including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

Exemplary Data Server Computing Entity

FIG. 2 provides a schematic of a data server computing entity 106 according to one embodiment of the present invention. In general, the terms computing entity, computer, entity, device, system, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Such functions, operations, and/or processes may include, for example, transmitting, receiving, operating on, processing, displaying, storing, determining, creating/generating, monitoring, evaluating, comparing, and/or similar terms used herein interchangeably. In one embodiment, these functions, operations, and/or processes can be performed on data, content, information, and/or similar terms used herein interchangeably.

As indicated, in one embodiment, the data server computing entity 106 may also include one or more communications interfaces 220 for communicating with various computing entities, such as by communicating data, content, information, and/or similar terms used herein interchangeably that can be transmitted, received, operated on, processed, displayed, stored, and/or the like.

As shown in FIG. 2, in one embodiment, the data server computing entity 106 may include, or be in communication with, one or more processing elements 205 (also referred to as processors, processing circuitry, and/or similar terms used herein interchangeably) that communicate with other elements within the data server computing entity 106 via a bus, for example. As will be understood, the processing element 205 may be embodied in a number of different ways.

For example, the processing element 205 may be embodied as one or more complex programmable logic devices (CPLDs), microprocessors, multi-core processors, coprocessing entities, application-specific instruction-set processors (ASIPs), microcontrollers, and/or controllers. Further, the processing element 205 may be embodied as one or more other processing devices or circuitry. The term circuitry may refer to an entirely hardware embodiment or a combination of hardware and computer program products. Thus, the processing element 205 may be embodied as integrated circuits, application specific integrated circuits (ASICs), field programmable gate arrays (FPGAs), programmable logic arrays (PLAs), hardware accelerators, other circuitry, and/or the like.

As will therefore be understood, the processing element 205 may be configured for a particular use or configured to execute instructions stored in volatile or non-volatile media or otherwise accessible to the processing element 205. As such, whether configured by hardware or computer program products, or by a combination thereof, the processing element 205 may be capable of performing steps or operations according to embodiments of the present invention when configured accordingly.

In one embodiment, the data server computing entity 106 may further include, or be in communication with, non-volatile media (also referred to as non-volatile storage, memory, memory storage, memory circuitry and/or similar terms used herein interchangeably). In one embodiment, the non-volatile storage or memory may include one or more non-volatile storage or memory media 210, including, but not limited to, hard disks, ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like.

As will be recognized, the non-volatile storage or memory media may store databases, database instances, database management systems, data, applications, programs, program modules, scripts, source code, object code, byte code, compiled code, interpreted code, machine code, executable instructions, and/or the like. The term database, database instance, database management system, and/or similar terms used herein interchangeably may refer to a collection of records or data that is stored in a computer-readable storage medium using one or more database models, such as a hierarchical database model, network model, relational model, entity-relationship model, object model, document model, semantic model, graph model, and/or the like.

In one embodiment, the data server computing entity 106 may further include, or be in communication with, volatile media (also referred to as volatile storage, memory, memory storage, memory circuitry and/or similar terms used herein interchangeably). In one embodiment, the volatile storage or memory may also include one or more volatile storage or memory media 215, including, but not limited to, RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like.

As will be recognized, the volatile storage or memory media may be used to store at least portions of the databases, database instances, database management systems, data, applications, programs, program modules, scripts, source code, object code, byte code, compiled code, interpreted code, machine code, executable instructions, and/or the like being executed by, for example, the processing element 205. Thus, the databases, database instances, database management systems, data, applications, programs, program modules, scripts, source code, object code, byte code, compiled code, interpreted code, machine code, executable instructions, and/or the like may be used to control certain aspects of the operation of the data server computing entity 106 with the assistance of the processing element 205 and operating system.

As indicated, in one embodiment, the data server computing entity 106 may also include one or more communications interfaces 220 for communicating with various computing entities, such as by communicating data, content, information, and/or similar terms used herein interchangeably that can be transmitted, received, operated on, processed, displayed, stored, and/or the like. Such communication may be executed using a wired data transmission protocol, such as fiber distributed data interface (FDDI), digital subscriber line (DSL), Ethernet, asynchronous transfer mode (ATM), frame relay, data over cable service interface specification (DOCSIS), or any other wired transmission protocol. Similarly, the data server computing entity 106 may be configured to communicate via wireless external communication networks using any of a variety of protocols, such as general packet radio service (GPRS), Universal Mobile Telecommunications System (UMTS), Code Division Multiple Access 2000 (CDMA2000), CDMA2000 1× (1×RTT), Wideband Code Division Multiple Access (WCDMA), Global System for Mobile Communications (GSM), Enhanced Data rates for GSM Evolution (EDGE), Time Division-Synchronous Code Division Multiple Access (TD-SCDMA), Long Term Evolution (LTE), Evolved Universal Terrestrial Radio Access Network (E-UTRAN), Evolution-Data Optimized (EVDO), High Speed Packet Access (HSPA), High-Speed Downlink Packet Access (HSDPA), IEEE 802.11 (Wi-Fi), Wi-Fi Direct, 802.16 (WiMAX), ultra-wideband (UWB), infrared (IR) protocols, near field communication (NFC) protocols, Wibree, Bluetooth protocols, wireless universal serial bus (USB) protocols, and/or any other wireless protocol.

Although not shown, the data server computing entity 106 may include, or be in communication with, one or more input elements, such as a keyboard input, a mouse input, a touch screen/display input, motion input, movement input, audio input, pointing device input, joystick input, keypad input, and/or the like. The data server computing entity 106 may also include, or be in communication with, one or more output elements (not shown), such as audio output, video output, screen/display output, motion output, movement output, and/or the like.

Exemplary Client Computing Entity

FIG. 3 provides an illustrative schematic representative of an client computing entity 102 that can be used in conjunction with embodiments of the present invention. In general, the terms device, system, computing entity, entity, and/or similar words used herein interchangeably may refer to, for example, one or more computers, computing entities, desktops, mobile phones, tablets, phablets, notebooks, laptops, distributed systems, kiosks, input terminals, servers or server networks, blades, gateways, switches, processing devices, processing entities, set-top boxes, relays, routers, network access points, base stations, the like, and/or any combination of devices or entities adapted to perform the functions, operations, and/or processes described herein. Client computing entities 102 can be operated by various parties. As shown in FIG. 3, the client computing entity 102 can include an antenna 312, a transmitter 304 (e.g., radio), a receiver 306 (e.g., radio), and a processing element 308 (e.g., CPLDs, microprocessors, multi-core processors, coprocessing entities, ASIPs, microcontrollers, and/or controllers) that provides signals to and receives signals from the transmitter 304 and receiver 306, correspondingly.

The signals provided to and received from the transmitter 304 and the receiver 306, correspondingly, may include signaling information/data in accordance with air interface standards of applicable wireless systems. In this regard, the client computing entity 102 may be capable of operating with one or more air interface standards, communication protocols, modulation types, and access types. More particularly, the client computing entity 102 may operate in accordance with any of a number of wireless communication standards and protocols, such as those described above with regard to the data server computing entity 106. In a particular embodiment, the client computing entity 102 may operate in accordance with multiple wireless communication standards and protocols, such as UMTS, CDMA2000, 1×RTT, WCDMA, GSM, EDGE, TD-SCDMA, LTE, E-UTRAN, EVDO, HSPA, HSDPA, Wi-Fi, Wi-Fi Direct, WiMAX, UWB, IR, NFC, Bluetooth, USB, and/or the like. Similarly, the client computing entity 102 may operate in accordance with multiple wired communication standards and protocols, such as those described above with regard to the data server computing entity 106 via a network interface 320.

Via these communication standards and protocols, the client computing entity 102 can communicate with various other entities using concepts such as Unstructured Supplementary Service Data (USSD), Short Message Service (SMS), Multimedia Messaging Service (MMS), Dual-Tone Multi-Frequency Signaling (DTMF), and/or Subscriber Identity Module Dialer (SIM dialer). The client computing entity 102 can also download changes, add-ons, and updates, for instance, to its firmware, software (e.g., including executable instructions, applications, program modules), and operating system.

According to one embodiment, the client computing entity 102 may include location determining aspects, devices, modules, functionalities, and/or similar words used herein interchangeably. For example, the client computing entity 102 may include outdoor positioning aspects, such as a location module adapted to acquire, for example, latitude, longitude, altitude, geocode, course, direction, heading, speed, universal time (UTC), date, and/or various other information/data. In one embodiment, the location module can acquire data, sometimes known as ephemeris data, by identifying the number of satellites in view and the relative positions of those satellites (e.g., using global positioning systems (GPS)). The satellites may be a variety of different satellites, including Low Earth Orbit (LEO) satellite systems, Department of Defense (DOD) satellite systems, the European Union Galileo positioning systems, the Chinese Compass navigation systems, Indian Regional Navigational satellite systems, and/or the like. This data can be collected using a variety of coordinate systems, such as the Decimal Degrees (DD); Degrees, Minutes, Seconds (DMS); Universal Transverse Mercator (UTM); Universal Polar Stereographic (UPS) coordinate systems; and/or the like. Alternatively, the location information/data can be determined by triangulating the client computing entity's 102 position in connection with a variety of other systems, including cellular towers, Wi-Fi access points, and/or the like. Similarly, the client computing entity 102 may include indoor positioning aspects, such as a location module adapted to acquire, for example, latitude, longitude, altitude, geocode, course, direction, heading, speed, time, date, and/or various other information/data. Some of the indoor systems may use various position or location technologies including RFID tags, indoor beacons or transmitters, Wi-Fi access points, cellular towers, nearby computing devices (e.g., smartphones, laptops) and/or the like. For instance, such technologies may include the iBeacons, Gimbal proximity beacons, Bluetooth Low Energy (BLE) transmitters, NFC transmitters, and/or the like. These indoor positioning aspects can be used in a variety of settings to determine the location of someone or something to within inches or centimeters.

The client computing entity 102 may also comprise a user interface (that can include a display 316 coupled to a processing element 308) and/or a user input interface (coupled to a processing element 308). For example, the user interface may be a user application, browser, user interface, and/or similar words used herein interchangeably executing on and/or accessible via the client computing entity 102 to interact with and/or cause display of information/data from the data server computing entity 106, as described herein. The user input interface can comprise any of a number of devices or interfaces allowing the client computing entity 102 to receive data, such as a keypad 318 (hard or soft), a touch display, voice/speech or motion interfaces, or other input device. In embodiments including a keypad 318, the keypad 318 can include (or cause display of) the conventional numeric (0-9) and related keys (#, *), and other keys used for operating the client computing entity 102 and may include a full set of alphabetic keys or set of keys that may be activated to provide a full set of alphanumeric keys. In addition to providing input, the user input interface can be used, for example, to activate or deactivate certain functions, such as screen savers and/or sleep modes.

The client computing entity 102 can also include volatile storage or memory 322 and/or non-volatile storage or memory 324, which can be embedded and/or may be removable. For example, the non-volatile memory may be ROM, PROM, EPROM, EEPROM, flash memory, MMCs, SD memory cards, Memory Sticks, CBRAM, PRAM, FeRAM, NVRAM, MRAM, RRAM, SONOS, FJG RAM, Millipede memory, racetrack memory, and/or the like. The volatile memory may be RAM, DRAM, SRAM, FPM DRAM, EDO DRAM, SDRAM, DDR SDRAM, DDR2 SDRAM, DDR3 SDRAM, RDRAM, TTRAM, T-RAM, Z-RAM, RIMM, DIMM, SIMM, VRAM, cache memory, register memory, and/or the like. The volatile and non-volatile storage or memory can store databases, database instances, database management systems, data, applications, programs, program modules, scripts, source code, object code, byte code, compiled code, interpreted code, machine code, executable instructions, and/or the like to implement the functions of the client computing entity 102. As indicated, this may include a user application that is resident on the entity or accessible through a browser or other user interface for communicating with the data server computing entity 106 and/or various other computing entities.

In another embodiment, the client computing entity 102 may include one or more components or functionality that are the same or similar to those of the data server computing entity 106, as described in greater detail above. As will be recognized, these architectures and descriptions are provided for exemplary purposes only and are not limiting to the various embodiments.

In various embodiments, the client computing entity 102 may be embodied as an artificial intelligence (AI) computing entity, such as an Amazon Echo, Amazon Echo Dot, Amazon Show, Google Home, and/or the like. Accordingly, the client computing entity 102 may be configured to provide and/or receive information/data from a user via an input/output mechanism, such as a display, a camera, a speaker, a voice-activated input, and/or the like. In certain embodiments, an AI computing entity may comprise one or more predefined and executable program algorithms stored within an onboard memory storage module, and/or accessible over a network. In various embodiments, the AI computing entity may be configured to retrieve and/or execute one or more of the predefined program algorithms upon the occurrence of a predefined trigger event.

V. EXEMPLARY SYSTEM OPERATIONS

FIG. 4 is a data flow diagram of an example process 400 for scalable dynamic transmission. Via the various steps/operations of the process 400, the data server computing entity 106 is configured to provide dynamically-generated data along with a predefined transactional response in response to a structured data request by a client computing entity 102 that specifies a predefined transactional inquiry.

The process 400 begins at step/operation 401 when the client computing entity 102 provides a structured data request to an application programming interface (API) gateway 411 of the data server computing entity 106. The client computing entity 102 may be a computing entity associated with a trading partner of an EDI server, such as with a hospital clinic, a medical provider, a health insurance claim clearing house, and/or the like in relation to a health insurance claim data EDI server. An operational example of a structured data request is an EDI 276 claim status request. Aspects of EDI 276 claim status requests are described in United Healthcare, Standard Companion Guide (Companion Guide Version Number 4.0, published Nov. 1, 2020), available online at https://www.uhcprovider.com/content/dam/provider/docs/public/resources/edi/EDI-276-277-Companion-Guide-005010X212.pdf.

The structured data request may describe one or more data fields of a request by a client computing entity 102 to obtain a structured data response that comprises a predefined transactional response, along with optionally one or more other data fields. The structured data request may include: (i) a structured request header that describes one or more general metadata fields associated with the structured data request, such as at least one of a requester identifier (e.g., an identifier of the trading partner) associated with the structured data request, a request type identifier (e.g., a request type identifier describing that the structured data request is an EDI 276 claim status request), a request time identifier (e.g., a request time identifier describing a generation time of the structured data request, a request time identifier describing a transmission time of the structured data request by the client computing entity, a request time identifier describing a receipt time of the structured data request by the data server computing entity, and/or the like); (ii) a structured request payload that describes a predefined transactional inquiry (e.g., a standardized transactional request, such as an EDI request including an EDI 276 claim status request) associated with the structured data request; and (iii) a structured request extension that may describe one or more extension request fields associated with the structured response field. In some embodiments, the predefined transactional inquiry specified by the structured request payload of the structured data request may be used to generate the predefined transactional response in the structured data response that is generated in response to the structured data request. In some embodiments, at least one of the one or more general metadata fields associated with the structured data request described by the structured request header or the one or more extension request fields described by the structured request extension may be used to generate a structured response extension of the structured data response that is generated in response to the structured data request.

As described above, the structured data request may include a structured request header, a structured request payload, and a structured request extension. The structured request header may describe a contiguous segment of a structured data request that describes one or more general metadata fields associated with the structured data request, wherein all valid structured data requests received by the data server computing entity 106 may be required by the data server computing entity 106 to describe acceptable values for all of the one or more "general" metadata fields. As such, the one or more general metadata fields described by the structured request header may correspond to properties of structured data requests that apply to different structured data requests having different structured data request types and being associated with different structured data requester profiles. Examples of such properties include: (i) a requester identifier that describes a structured requester profile associated with a structured data request (e.g., a requester identifier that describes an identifier of the trading partner associated with the structured data request), (ii) a request type identifier that describes a structured data request type associated with a structured data request (e.g., a request type identifier that describes that a structured data request is an EDI 276 claim status request), and (iii) a request time identifier that describes a structured data request time associated with the structured data request (e.g., a request time identifier that describes a generation time of the structured data request, a request time identifier describing a transmission time of the structured data request by the client computing entity, a request time identifier describing a receipt time of the structured data request by the data server computing entity, and/or the like).

A structured request payload may describe a continuous segment (e.g., a defined payload data field) of a structured data request that describes a predefined transactional inquiry associated with the structured data request, where the predefined transactional inquiry is a transactional inquiry that is formatted in accordance with a transactional inquiry/response formatting scheme such as a standardized transactional inquiry/response formatting scheme. An example of a standardized transactional inquiry/response formatting scheme is an EDI transactional inquiry/response formatting scheme, and examples of predefined transactional inquiries that may be generated using the EDI transactional inquiry/response formatting scheme include an EDI 276 predefined transactional inquiry, aspects of which are described in United Healthcare, Standard Companion Guide (Companion Guide Version Number 4.0, published Nov. 1, 2020), available online at https://www.uhcprovider.com/content/dam/provider/docs/public/resources/edi/EDI-276-277-Companion-Guide-005010X212.pdf. In some embodiments, the predefined transactional inquiry is an EDI inquiry. In some of the noted embodiments, the EDI inquiry is an EDI 276 inquiry. In some embodiments, an identifier (e.g., a numeric identifier) of a request type of the predefined transactional inquiry (e.g., as defined by the corresponding transactional inquiry/response formatting scheme and/or as defined by the data server computing entity) is provided as part of the general metadata fields described by the structured request header of the structured data request to which the structured request payload belongs (e.g., as the request type identifier of the structured request header of the structured data request to which the structured request payload belongs). While various embodiments of the present invention are described with reference to an exemplary embodiment in which a structured data request describes one predefined transactional inquiry only, a person of ordinary skill in the relevant technology will recognize that a structured request payload may in some embodiments describe two or more predefined transactional inquiries without departing from the spirit of the present invention.

A structured request extension may describe a contiguous segment of a structured data request that may optionally describe one or more extension request fields associated with the structured data request. The structured request extension may enable a client computing entity 102 to explicitly request data beyond the data provided in response to a predefined transactional inquiry described by the structured request payload of the structured data request. Importantly, however, the structured request extension may in some embodiments describe no extension requests fields (i.e., "is empty"), in order to enable the client computing entity to make requests for predefined transactional responses via predefined transactional inquiries without explicitly specifying extension request fields. In some embodiments, even when the structured request extension of a structured data response is empty such that no extension requests fields are specified by the structured request extension, a structured response extension of a structured data response generated in response to the structured data response may include extension response fields (e.g., may be "non-empty"). This may be because, in at least some embodiments, the extension response fields described by a structured response extension of a structured data response may include static extension response fields determined based on the one or more extension request fields described by a structured request extension of a corresponding structured data request as well as dynamic extension response fields determined based on a subset of the general metadata fields described by the structured request header of the corresponding structured data request.

An operational example of a structured data request 500 is depicted in FIG. 5. As depicted in FIG. 5, the structured data request includes the structured request header 501, the structured request payload 502, and the structured request extension 503. As described above, the structured request header 501 may be a contiguous segment of the structured data request 500 that describes one or more general metadata fields associated with the structured data request 500. Examples of such general metadata fields include the requester identifier 511 and the request type identifier 512.

As further described above, the structured request payload 502 may be a continuous segment of the structured data request 500 that describes a predefined transactional inquiry 513 associated with the structured data request 500. As depicted in FIG. 5, the predefined transactional inquiry 513 is an EDI 276 predefined transactional inquiry that is a claim status inquiry formatted in accordance with the formatting schemes of the EDI standard.

As further described above, the structured request extension 503 may be a contiguous segment of the structured data request 500 that may optionally describe one or more extension request fields associated with the structured data request 500. As depicted in FIG. 5, the extension request fields described by the structured request extension 503 describe requests for claim status information and coordination of benefits (COB) information associated with a health insurance claim described by the predefined transactional inquiry 513. Other examples of extension request fields include extension request fields that describes requests for claim check of a health insurance claim described by the predefined transactional inquiry 513.

Returning to FIG. 4, subsequent to receiving the structured data request at step/operation 401, step/operation 402, the API gateway 411 queries a structured data retrieval service 412 of the data server computing 106 to process the predefined transactional inquiry described by the structured request payload of the structured data request to generate a structured response payload, and subsequently receives the structured response payload from the structured data retrieval service 412 in response to the query. For example, the structured data retrieval service 412 may be an EDI service that is configured to process EDI requests (e.g., EDI 276 claim status requests) to generate responsive EDI responses (e.g., EDI 277 claim status responses). Accordingly, in some embodiments, the structured data retrieval service 412 may be configured to have a static logic that is configured to process structured data requests in a uniform manner irrespective of general properties of structured data requests as specified by structured requester headers and/or irrespective of extension requests described by structured data extensions. This in turn enables the data server computing entity 106 to limit the portions of the data exchange logic of the data server computing entity 106 that need to be modified to enable dynamic data exchange in a scalable fashion.

As discussed above, the structured data retrieval service 412 of the data server computing 106 may be configured to process the predefined transactional inquiry described by the structured request payload of the structured data request to generate a structured response payload. A structured response payload may describe a contiguous segment of a structured data response that describes a predefined transactional response associated with the structured data response, where the predefined transactional response is a transactional response that is formatted in accordance with a transactional inquiry/response formatting scheme such as a standardized transactional inquiry/response formatting scheme. An example of a standardized transactional inquiry/response formatting scheme is an EDI transactional inquiry/response formatting scheme, and examples of predefined transactional inquiries that may be generated using the EDI transactional inquiry/response formatting scheme include an EDI 277 predefined transactional response, aspects of which are described in United Healthcare, Standard Companion Guide (Companion Guide Version Number 4.0, published Nov. 1, 2020), available online at https://www.uhcprovider.com/content/dam/provider/docs/public/resources/edi/EDI-276-277-Companion-Guide-005010X212.pdf. In some embodiments, the predefined transactional response is an EDI response. In some of the noted embodiments, the EDI response is an EDI 277 claim status response. In some embodiments, an identifier (e.g., a numeric identifier) of a response type of the predefined transactional response (e.g., as defined by the corresponding transactional inquiry/response formatting scheme and/or as defined by the data server computing entity) is provided as part of general metadata fields described by a structured response payload of the structured data response to which the structured response payload belongs (e.g., as the response type identifier of the structured response header of the structured data response to which the structured response payload belongs). While various embodiments of the present invention are described with reference to an exemplary embodiment in which a structured data request describes one predefined transactional inquiry only, a person of ordinary skill in the relevant technology will recognize that a structured request payload may in some embodiments describe two or more predefined transactional inquiries without departing from the spirit of the present invention. In some of those embodiments, when the structured request payload of a structured data request describes two or more predefined transactional inquiries, the structured response payload of a structured data response that is generated in response to the structured data request describes two or more predefined transactional responses (e.g., a predefined transactional response corresponding to each of the two or more predefined transactional inquiries).

In some embodiments, segments/fields of the predefined transactional response of a structured data request can be related to sections of the structured response extension of a corresponding structured data response using designators in the structured response extension, e.g., using key data structures in the structured response extension. For example, in the structured data response 1000 of FIG. 10, the following values from the predefined transactional response 1001 appear in the key structure 1011 of the structured response extension 1002: 9918046987, 897327846920, 20200122, and 372. As another example, in the structured data response 1000 of FIG. 10, the following values from the predefined transactional response 1001 appear in the key structure 1012 of the structured response extension 1002: 3877537099Z1 and 372. As predefined transactional responses get more complex, this functionality can be critical as it allows for the ability to tie data in the structured response extensions to correct entities (e.g., claims, service lines, and/or the like) described by the predefined transactional responses.

In some embodiments, the predefined transactional response is determined based at least in part on one or more selection criteria defined in the structured request extension of the structured data response. For example, as depicted in FIG. 9, the structured request extension 900 includes two selection criteria each expressed as a collection of two key-value pairs: a selection criterion 901 defined based on a particular procedure code value for a procedure code property, and a selection criterion 902 based on a particular diagnosis code value for a diagnosis code property. In some embodiments, the data server computing entity 106 processes the two noted selection criteria in the structured request extension 900 to include, as part of the predefined transactional response, claim information for claims that satisfy (e.g., among one or more other conditions corresponding to properties specified in the predefined transactional request for a structured request payload of a corresponding structured request payload) a condition defined based on the procedure code property and a condition defined based on the diagnosis code property. In some embodiments, the data server computing entity 106 processes the two noted selection criteria in the structured request extension 900 to exclude, from the predefined transactional response, claim information for claims that fail to satisfy a condition defined based on the procedure code property or a condition defined based on the diagnosis code property.

In addition to steps/operation 402, subsequent to receiving the structured data request at step/operation 401, at step/operation 403, the API gateway 411 queries the storage subsystem 108 to obtain extension response fields and generates the structured data response based on the extension response fields and the structured response payload. For example, the API gateway 411 may query a backend storage component of the storage subsystem 108 to obtain extension response fields and proceed to generate the structured data response based on the extension response fields and the structured response payload.

In some embodiments, step/operation 403 may be performed in accordance with the process that is depicted in FIG. 6. The process that is depicted in FIG. 6 begins at step/operation 601 when the API gateway 411 determines (e.g., identifies and retrieves from the storage subsystem 108) one or more dynamic extension response fields based on the structured request header. As described above, the structured request header may describe a contiguous segment of a structured data request that describes one or more general metadata fields associated with the structured data request, wherein all valid structured data requests received by the data server computing entity 106 may be required by the data server computing entity 106 to describe acceptable values for all of the one or more "general" metadata fields. As such, the one or more general metadata fields described by the structured request header may correspond to properties of structured data requests that apply to different structured data requests having different structured data request types and being associated with different structured data requester profiles. Examples of such properties include: (i) a requester identifier that describes a structured requester profile associated with a structured data request (e.g., a requester identifier that describes an identifier of the trading partner associated with the structured data request), (ii) a request type identifier that describes a structured data request type associated with a structured data request (e.g., a request type identifier that describes that a structured data request is an EDI 276 claim status request), and (iii) a request time identifier that describes a structured data request time associated with the structured data request (e.g., a request time identifier that describes a request time identifier describing a generation time of the structured data request, a request time identifier describing a transmission time of the structured data request by the client computing entity, a request time identifier describing a receipt time of the structured data request by the data server computing entity, and/or the like).

In some embodiments, at step/operation 601, the API gateway 411 is configured to generate a dynamically-generated portion of the extension response fields of a structured response extension of a structured data response based on at least a portion (e.g., one or more of) the general metadata fields described by the structured request header of the corresponding structured data request for the structured data response. This may enable the data server computing entity 106 to provide different extension response fields in response to different structured data requests based on properties of the structured data requests as described by the structured request headers of the noted structured data requests.

For example, the API gateway 411 may be configured to generate at least some of the dynamic response extension data fields of a structured response extension of a structured data response based on a requester identifier of the corresponding structured data request. This may in turn enable the data server computing entity 106 to: (i) provide a first set of dynamic extension data fields as part of structured data responses generated in response to structured data requests by a first requester identifier, and (ii) provide a second set of dynamic extension data fields that is different from the first set of dynamic extension data fields as part of structured data responses generated in response to structured data requests by a second requester identifier.

As another example, the API gateway 411 may be configured to generate at least some of the dynamic response extension data fields of a structured response extension of a structured data response based on a request type identifier of the corresponding structured data request. This may in turn enable the data server computing entity 106 to: (i) provide a first set of dynamic extension data fields as part of structured data responses generated in response to structured data fields having a first request type identifier, and (ii) provide a second set of dynamic extension data fields that is different from the first set of dynamic extension data fields as part of structured data responses generated in response to structured data fields having a second request type identifier.

As yet another example, the API gateway 411 may be configured to generate at least some of the dynamic response extension data fields of a structured response extension of a structured data response based on a request time identifier of the corresponding structured data request. This may in turn enable the data server computing entity 106 to: (i) provide a first set of dynamic extension data fields as part of structured data responses generated in response to structured data fields having a first request time identifier, and (ii) provide a second set of dynamic extension data fields that is different from the first set of dynamic extension data fields as part of structured data responses generated in response to structured data fields having a second request time identifier.

As a further example, API gateway 411 may be configured to generate at least some of the dynamic response extension data fields of a structured response extension of a structured data response based on a requester identifier of the corresponding structured data request and a request type identifier of the corresponding structured data request. This may in turn enable the data server computing entity 106 to: (i) provide a first set of dynamic extension data fields as part of structured data responses generated in response to structured data requests by a first requester identifier that have a first request type identifier, (ii) provide a second set of dynamic extension data fields (that is different from the first set of dynamic extension data fields) as part of structured data responses generated in response to structured data requests by a first requester identifier that have a second request type identifier, (iii) provide a third set of dynamic extension data fields (that is different from the first set of dynamic extension data fields and the second set of dynamic extension data fields) as part of structured data responses generated in response to structured data requests by a second requester identifier that have a first request type identifier, and (iv) provide a fourth set of dynamic extension data fields (that is different from the first set of dynamic extension data fields, the second set of dynamic extension data fields, and the third set of dynamic extension data fields) as part of structured data responses generated in response to structured data requests by a second requester identifier that have a second request type identifier.

As another example, API gateway 411 may be configured to generate at least some of the dynamic response extension data fields of a structured response extension of a structured data response based on a requester identifier of the corresponding structured data request and a request time identifier of the corresponding structured data request. This may in turn enable the data server computing entity 106 to: (i) provide a first set of dynamic extension data fields as part of structured data responses generated in response to structured data requests by a first requester identifier that have a first request time identifier, (ii) provide a second set of dynamic extension data fields (that is different from the first set of dynamic extension data fields) as part of structured data responses generated in response to structured data requests by a first requester identifier that have a second request time identifier, (iii) provide a third set of dynamic extension data fields (that is different from the first set of dynamic extension data fields and the second set of dynamic extension data fields) as part of structured data responses generated in response to structured data requests by a second requester identifier that have a first request time identifier, and (iv) provide a fourth set of dynamic extension data fields (that is different from the first set of dynamic extension data fields, the second set of dynamic extension data fields, and the third set of dynamic extension data fields) as part of structured data responses generated in response to structured data requests by a second requester identifier that have a second request time identifier.

As a further example, API gateway 411 may be configured to generate at least some of the dynamic response extension data fields of a structured response extension of a structured data response based on a request identifier of the corresponding structured data request, a request type identifier of the corresponding structured data object, and a request time identifier of the corresponding structured data request. This may in turn enable the data server computing entity 106 to: (i) provide a first set of dynamic extension data fields as part of structured data responses generated in response to structured data requests by a first requester identifier that have a first request type identifier and a first request time identifier, (ii) provide a second set of dynamic extension data fields (that is different from the first set of dynamic extension data fields) as part of structured data responses generated in response to structured data requests by a first requester identifier that have a first request type identifier and a second request time identifier, (iii) provide a third set of dynamic extension data fields (that is different from the first set of dynamic extension data fields and the second set of dynamic extension data fields) as part of structured data responses generated in response to structured data requests by a first requester identifier that have a second request type identifier and a first request time identifier, (iv) provide a fourth set of dynamic extension data fields (that is different from the first set of dynamic extension data fields, the second set of dynamic extension data fields, and the third set of dynamic extension data fields) as part of structured data responses generated in response to structured data requests by a first requester identifier that have a second request type identifier and second request time identifier, (v) provide a fifth set of dynamic extension data fields (that is different from the first set of dynamic extension data fields, the second set of dynamic extension data fields, the third set of dynamic extension data fields, and the fourth set of dynamic extension data fields) as part of structured data responses generated in response to structured data requests by a second requester identifier that have a first request type identifier and a first request time identifier, (vi) provide a sixth set of dynamic extension data fields (that is different from the first set of dynamic extension data fields, the second set of dynamic extension data fields, the third set of dynamic extension data fields, the fourth set of dynamic extension data fields, and the fifth set of dynamic extension data fields) as part of structured data responses generated in response to structured data requests by a second requester identifier that have a first request type identifier and a second request time identifier, (vii) provide a seventh set of dynamic extension data fields (that is different from the first set of dynamic extension data fields, the second set of dynamic extension data fields, the third set of dynamic extension data fields, the fourth set of dynamic extension data fields, the fifth set of dynamic extension data fields, and the sixth set of dynamic extension data fields) as part of structured data responses generated in response to structured data requests by a first requester identifier that have a second request type identifier and a first request time identifier, and (viii) provide an eighth set of dynamic extension data fields (that is different from the first set of dynamic extension data fields, the second set of dynamic extension data fields, the third set of dynamic extension data fields, the fourth set of dynamic extension data fields, the fifth set of dynamic extension data fields, the sixth set of dynamic extension data fields, and the seventh set of dynamic extension data fields) as part of structured data responses generated in response to structured data requests by a second requester identifier that have a second request type identifier and second request time identifier.

In general, a dynamic extension response field may be a data field included in a structured data response based on a general metadata property of a corresponding structured data request as described by a structured request header of the structured data request. In some embodiments, to generate the dynamic extension response fields in response to a structured data request, a data server computing entity: (i) identifies a predefined number of dynamic context metadata fields of the structured request header of the structured data request as defined by configuration data of the data server computing entity, (ii) queries a repository of dynamic contexts based on the dynamic context metadata fields to determine a dynamic context of the structured data request, and (iii) determines the dynamic extension response fields based on a set of dynamic response extension fields associated with the dynamic context.

In some embodiments, step/operation 601 may be performed in accordance with the process that is depicted in FIG. 7. The process that is depicted in FIG. 7 begins at step/operation 701 when the API gateway 411 identifies a predefined number of dynamic context metadata fields of the structured request header of the structured data request as defined by configuration data of the data server computing entity 106. A dynamic context metadata field may be a metadata field described by a structured request header of the structured data request that may be used to infer dynamic response extension fields for a corresponding structured data response. For example, in an embodiment in which different sets of dynamic extension response fields are defined for different requester identifiers, the predefined number of dynamic context metadata fields may include the requester identifier field. As another example, in an embodiment in which different sets of dynamic extension response fields are defined for different request type identifiers, the predefined number of dynamic context metadata fields may include the request type identifier field. As a further example, in an embodiment in which different sets of dynamic extension response fields are defined for different request time identifiers, the predefined number of dynamic context metadata fields may include the request time identifier field. As a further example, in an embodiment in which different sets of dynamic extension response fields are defined for different requester identifiers and/or different request type identifiers, the predefined number of dynamic context metadata fields may include the requester identifier field and the request type identifier field. As an additional example, in an embodiment in which different sets of dynamic extension response fields are defined for different requester identifiers, different request type identifiers, and/or different request time identifiers, the predefined number of dynamic context metadata fields may include the requester identifier field, the request type identifier field, and the request time identifier field.

At step/operation 702, the API gateway 411 identifies a repository of candidate dynamic contexts. A dynamic context may be a combination of the data field values for a subset of the predefined number of dynamic context metadata fields that is assigned to a set of dynamic response extension fields. For example, if the predefined number of dynamic context metadata fields include the requester identifier field, then the dynamic contexts may include: (i) a dynamic context associated with the requester identifier RI1, (ii) a dynamic context associated with the requester identifier RI2, and (iii) a dynamic context associated with the requester identifier RI3. As another example, if the predefined number of dynamic context metadata fields include the requester identifier field, the request type identifier field, and the request time identifier field, then the candidate dynamic contexts may include: (i) a candidate dynamic context associated with the requester identifier RI1, (ii) a candidate dynamic context associated with the requester identifier RI1 and the request type identifier RTPI1, (iii) a candidate dynamic context associated with the requester identifier RI2 and the request time identifier RTMI1, and (iv) a candidate dynamic context associated with the requester identifier RI1, the request type identifier RTPI1, and the request time identifier RTMI2. In some embodiments, the dynamic contexts are generated based on detected frequent historical request activity patterns data recorded by the data server computing entity 106.

At step/operation 703, the API gateway 411 determines the dynamic context for the structured data request based on the predefined number of dynamic context metadata fields of the structured request header of the structured data request and the repository of candidate dynamic contexts. In some embodiments, to select the dynamic context for a structured data request, the API gateway 411 first identifies the candidate dynamic contexts that match all of the predefined number of dynamic context metadata fields for the structured data request and then selects the candidate dynamic context having the highest match score with respect to the structured data request.

For example, consider a repository of candidate dynamic contexts that includes: (i) a candidate dynamic context associated with the requester identifier RI1, (ii) a candidate dynamic context associated with the requester identifier RI1 and the request type identifier RTPI1, (iii) a candidate dynamic context associated with the requester identifier RI2 and the request time identifier RTMI1, and (iv) a candidate dynamic context associated with the requester identifier RI1, the request type identifier RTPI1, and the request time identifier RTMI2. Given a structured data request that is associated with the requester identifier RI1, the request type identifier RTPI1, and the request time identifier RTMI2 as the predefined number of dynamic context metadata fields, the following candidate dynamic contexts match the structured data request: the first candidate dynamic context, the second candidate dynamic context, and the fourth candidate dynamic context. Among the three noted candidate dynamic contexts, the first candidate dynamic context has a match score of one (as it only matches one of the predefined number of dynamic context metadata fields of the structured data request), the second candidate dynamic context has a match score of two (as it only matches two of the predefined number of dynamic context metadata fields of the structured data request), and the fourth candidate dynamic context has a match score of three (as it matches three of the predefined number of dynamic context metadata fields of the structured data request). Accordingly, in at least some embodiments, because the fourth candidate dynamic context has the highest match score, the fourth candidate dynamic context may be selected as the dynamic context for the structured data request that is associated with the requester identifier RI1, the request type identifier RTPI1, and the request time identifier RTMI2 as the predefined number of dynamic context metadata fields.

At step/operation 704, the API gateway 411 determines the dynamic extension response fields based on the dynamic context. In some embodiments, the API gateway 411 retrieves the data value for each dynamic extension response field type described by the set of dynamic extension response fields associated with the dynamic context, and uses the noted data values to generate the dynamic extension response fields.

Returning to FIG. 6, at step/operation 602, the API gateway 411 determines static extension response fields based on the structured request extension of the structured data response. A static extension response field may be a data field included in a structured data response based on a structured request extension field of a structured request extension of a corresponding structured data request. As described above, a structured request extension may describe a contiguous segment of a structured data request that may optionally describe one or more extension request fields associated with the structured data request. The structured request extension may enable a client computing entity 102 to explicitly request data beyond the data provided in response to a predefined transactional inquiry described by the structured request payload of the structured data request.

At step/operation 603, the API gateway 411 generates the structured data response based on the static extension response fields and the dynamic extension response fields. In some embodiments, the static extension response fields and the dynamic extension response fields are among the extension response fields that are included in a structured response extension of the structured data response. The structured data response may also include at least one of a structured response header and a structured response payload.

The structured data response may describe one or more data fields of a response by a data server computing entity 106 to a structured data request by a client computing entity 102, where the one or more data fields comprise a predefined transactional response to a predefined transactional inquiry described by the structured data request, along with one or more optional other fields. The structured data response may include: (i) a structured response header that describes one or more general metadata fields associated with the structured data response and/or the corresponding structured data request, such as at least one of a requester identifier (e.g., an identifier of the trading partner) associated with the structured data request, a response type identifier (e.g., a response type identifier describing that the structured data response is an EDI 277 claim status response), a response time identifier (e.g., a response time identifier describing a generation time of the structured data response, a response time identifier describing a transmission time of the structured data response by the data server computing entity, and/or the like); (ii) a structured response payload that describes a predefined transactional response (e.g., a standardized transactional response, such as an EDI response including an EDI 277 claim status response) associated with the structured data response; and (iii) a structured response extension that may describe one or more extension response fields associated with the structured response field. In some embodiments, the predefined transactional response specified by the structured response payload of the structured data response may be generated based on the predefined transactional inquiry in the corresponding structured data request.

As described above, the structured data response may include a structured response header, a structured response payload, and a structured response extension. The structured response header may describe a contiguous segment of a structured data response that describes one or more general metadata fields associated with the structured data response and/or the corresponding structured data request, wherein all valid structured data responses generated by the data server computing entity 106 may be required by the data server computing entity 106 to describe acceptable values for all of the one or more "general" metadata fields. As such, the one or more general metadata fields described by the structured response header may correspond to properties of structured data requests and/or structured data responses that apply to different structured data requests and/or different structured data responses having different structured data request types and/or having different structured data response types and being associated with different structured data requester profiles. Examples of such properties include: (i) a requester identifier that describes a structured requester profile associated with a corresponding structured data request (e.g., a requester identifier that describes an identifier of the trading partner associated with the structured data request), (ii) a response type identifier that describes a structured data response type associated with a structured data response (e.g., a response type identifier that describes that a structured data response is an EDI 277 claim status response), and (iii) a response time identifier that describes a structured data response time associated with the structured data response (e.g., a response time identifier that describes a generation time of the structured data response, a request time identifier describing a transmission time of the structured data response, and/or the like).

The structured response payload may describe a contiguous segment of a structured data response that describes a predefined transactional response associated with the structured data response, where the predefined transactional response is a transactional response that is formatted in accordance with a transactional inquiry/response formatting scheme such as a standardized transactional inquiry/response formatting scheme. An example of a standardized transactional inquiry/response formatting scheme is an EDI transactional inquiry/response formatting scheme, and examples of predefined transactional inquiries that may be generated using the EDI transactional inquiry/response formatting scheme include an EDI 277 predefined transactional response, aspects of which are described in United Healthcare, Standard Companion Guide (Companion Guide Version Number 4.0, published Nov. 1, 2020), available online at https://www.uhcprovider.com/content/dam/provider/docs/public/resources/edi/EDI-276-277-Companion-Guide-005010X212.pdf. In some embodiments, the predefined transactional response is an EDI response. In some of the noted embodiments, the EDI response is an EDI 277 claim status response. In some embodiments, an identifier (e.g., a numeric identifier) of a response type of the predefined transactional response (e.g., as defined by the corresponding transactional inquiry/response formatting scheme and/or as defined by the data server computing entity) is provided as part of general metadata fields described by a structured response payload of the structured data response to which the structured response payload belongs (e.g., as the response type identifier of the structured response header of the structured data response to which the structured response payload belongs). While various embodiments of the present invention are described with reference to an exemplary embodiment in which a structured data request describes one predefined transactional inquiry only, a person of ordinary skill in the relevant technology will recognize that a structured request payload may in some embodiments describe two or more predefined transactional inquiries without departing from the spirit of the present invention. In some of those embodiments, when the structured request payload of a structured data request describes two or more predefined transactional inquiries, the structured response payload of a structured data response that is generated in response to the structured data request describes two or more predefined transactional responses (e.g., a predefined transactional response corresponding to each of the two or more predefined transactional inquiries).

The structured response extension may describe a continuous segment of a structured data response that describes one or more extension response fields of the structured data response. In some embodiments, the extension response fields described by a structured response extension of a structured data response may include at least one of static extension response fields determined based on the one or more extension request fields described by a structured request extension of a corresponding structured data request or dynamic extension response fields determined based on a subset of the general metadata fields described by the structured request header of the corresponding structured data request. In some embodiments, the structured request extension may enable a client computing entity 102 to explicitly request data beyond the data provided in response to a predefined transactional inquiry described by the structured request payload of the structured data request. In some of the noted embodiments, these data requests (aka. "request extension data fields) are used to determine static extension response fields of the structured response extension.

An operational example of a structured data response 800 is depicted in FIG. 8. As depicted in FIG. 8, the structured data response 800 includes the structured response header 801, the structured response payload 802, and the structured response extension 803.

As described above, the structured response header 801 may be a contiguous segment of the structured data response 800 that describes one or more general metadata fields associated with the structured data response 800 and/or with the corresponding structured data requests. Examples of such general metadata fields include the requester identifier 811 and the response type identifier 812.

As further described above, the structured response payload 802 may be a continuous segment of the structured data response 800 that describes a predefined transactional response 813 associated with the structured data response 800. As depicted in FIG. 8, the predefined transactional response 813 is an EDI 277 predefined transactional response that is a claim status inquiry response formatted in accordance with the formatting schemes of the EDI standard.

As further described above, the structured response extension 803 may be a contiguous segment of the structured data response 800 that may optionally describe one or more extension response fields associated with the structured data response 800. As depicted in FIG. 8, the extension response fields described by the structured response extension 803 describe various claim information beyond the information provided in the structured response payload 802.

Returning to FIG. 4, subsequent to generating the structured data response at step/operation 403, at step/operation 404, the data server computing entity 106 transmits the structured data response to the client computing entity 102. The client computing entity 102 may be configured to perform one or more response-based actions based on the structured data response, for example displaying a data reporting user interface that describes at least one of the predefined transactional response of the structured response payload of the structured data response or one or more of the response extension fields described by the structured response extension of the structured data response.

VI. CONCLUSION

Many modifications and other embodiments will come to mind to one skilled in the art to which this disclosure pertains having the benefit of the teachings presented in the foregoing descriptions and the associated drawings. Therefore, it is to be understood that the disclosure is not to be limited to the specific embodiments disclosed and that modifications and other embodiments are intended to be included within the scope of the appended claims. Although specific terms are employed herein, they are used in a generic and descriptive sense only and not for purposes of limitation.

The invention claimed is:

1. A computer-implemented method for scalable dynamic data transmission, the computer-implemented method comprising:
    identifying, using one or more processors, a structured data request, wherein: (i) the structured data request comprises a structured request header, a structured request payload, and a structured request extension, (ii) the structured request header describes a requester identifier and one or more metadata fields, (iii) the structured request payload describes a predefined transactional inquiry, and (iv) the structured request header, the structured request payload, and the structured request extension comprise separate segments of the structured data request;
    determining, using the one or more processors and based at least in part on the predefined transactional inquiry, a predefined transactional response associated with the structured data request;
    determining, using the one or more processors and based at least in part on the structured request extension and the requester identifier, one or more extension response fields comprising one or more dynamic extension response fields that are identified by querying a repository of dynamic contexts based at least in part on the requester identifier and the one or more metadata fields;
    generating, using the one or more processors, a structured data response for the structured data request, wherein: (i) the structured data response comprises a structured response payload and a structured response extension, (ii) the structured response payload describes the predefined transactional response, and (iii) the structured response extension describes the one or more extension response fields; and
    causing, using the one or more processors, the structured data response to be transmitted to a client computing entity, wherein the client computing entity is configured to perform one or more response-based actions based at least in part on the structured data response.

2. The computer-implemented method of claim 1, wherein:
the one or more extension response fields further comprise one or more static extension response fields,
the structured request extension describes one or more static extension inquiries, and
the one or more static extension response fields are determined based at least in part on the one or more static extension inquiries.

3. The computer-implemented method of claim 1, wherein:
the structured request header further describes a request type identifier; and
the one or more dynamic extension response fields are determined based at least in part on the requester identifier and the request type identifier.

4. The computer-implemented method of claim 1, wherein:
the structured request header further describes a request type identifier; and
the one or more dynamic extension response fields are determined based at least in part on the requester identifier and the request type identifier.

5. The computer-implemented method of claim 3, wherein:
the structured data response further comprises a structured response header, and
the structured response header describes the request type identifier.

6. The computer-implemented method of claim 1, wherein the predefined transactional inquiry is an electronic data interchange (EDI) inquiry.

7. The computer-implemented method of claim 6, wherein the EDI inquiry is an EDI 276 inquiry.

8. The computer-implemented method of claim 1, wherein the predefined transactional inquiry is an electronic data interchange (EDI) response.

9. The computer-implemented method of claim 8, wherein the EDI response is an EDI 277 claim status response.

10. The computer-implemented method of claim 1, wherein:
the one or more dynamic extension response fields are determined based at least in part on a dynamic context of the structured data request, and
the dynamic context is determined based at least in part on a predefined number of dynamic context metadata fields of the structured request header of the structured data response request.

11. A computing system comprising one or more processors and memory including program code, the memory and the program code configured to, with the one or more processors, cause the computing system to at least:
identify a structured data request, wherein: (i) the structured data request comprises a structured request header, a structured request payload, and a structured request extension, (ii) the structured request header describes a requester identifier and one or more metadata fields, (iii) the structured request payload describes a predefined transactional inquiry, and (iv) the structured request header, the structured request payload, and the structured request extension comprise separate segments of the structured data request;
determine, based at least in part on the predefined transactional inquiry, a predefined transactional response associated with the structured data request;
determine based at least in part on the structured request extension and the requester identifier, one or more extension response fields comprising one or more dynamic extension response fields that are identified by querying a repository of dynamic contexts based at least in part on the requester identifier and the one or more metadata fields;
generate a structured data response for the structured data request, wherein: (i) the structured data response comprises a structured response payload and a structured response extension, (ii) the structured response payload describes the predefined transactional response, and (iii) the structured response extension describes the one or more extension response fields; and
cause the structured data response to be transmitted to a client computing entity, wherein the client computing entity is configured to perform one or more response-based actions based at least in part on the structured data response.

12. The computing system of claim 11, wherein:
the one or more extension response fields further comprise one or more static extension response fields,
the structured request extension describes one or more static extension inquiries, and
the one or more static extension response fields are determined based at least in part on the one or more static extension inquiries.

13. The computing system of claim 11, wherein:
the structured request header further describes a request type identifier; and
the one or more dynamic extension response fields are determined based at least in part on the requester identifier and the request type identifier.

14. The computing system of claim 11, wherein:
the structured request header further describes a request time identifier; and
the one or more dynamic extension response fields are determined based at least in part on the requester identifier and the request time identifier.

15. The computing system of claim 13, wherein:
the structured data response further comprises a structured response header, and
the structured response header describes the request type identifier.

16. A computer program product comprising at least one non-transitory computer-readable storage medium having computer-readable program code portions stored therein, the computer-readable program code portions configured to:
identify a structured data request, wherein: (i) the structured data request comprises a structured request header, a structured request payload, and a structured request extension, (ii) the structured request header describes a requester identifier and one or more metadata fields, (iii) the structured request payload describes a predefined transactional inquiry, and (iv) the structured request header, the structured request payload, and the structured request extension comprise separate segments of the structured data request;
determine, based at least in part on the predefined transactional inquiry, a predefined transactional response associated with the structured data request;
determine based at least in part on the structured request extension and the requester identifier, one or more extension response fields comprising one or more dynamic extension response fields that are identified by querying a repository of dynamic contexts based at least in part on the requester identifier and the one or more metadata fields;

generate a structured data response for the structured data request, wherein: (i) the structured data response comprises a structured response payload and a structured response extension, (ii) the structured response payload describes the predefined transactional response, and (iii) the structured response extension describes the one or more extension response fields; and cause the structured data response to be transmitted to a client computing entity, wherein the client computing entity is configured to perform one or more response-based actions based at least in part on the structured data response.

17. The computer program product of claim 16, wherein:
the one or more extension response fields further comprise one or more static extension response fields, the structured request extension describes one or more static extension inquiries, and
the one or more static extension response fields are determined based at least in part on the one or more static extension inquiries.

18. The computer program product of claim 16, wherein:
the structured request header further describes a request type identifier; and
the one or more dynamic extension response fields are determined based at least in part on the requester identifier and the request type identifier.

19. The computer program product of claim 16, wherein:
the structured request header further describes a request time identifier; and
the one or more dynamic extension response fields are determined based at least in part on the requester identifier and the request time identifier.

* * * * *

UNITED STATES PATENT AND TRADEMARK OFFICE
CERTIFICATE OF CORRECTION

PATENT NO. : 12,080,389 B2  
APPLICATION NO. : 17/162627  
DATED : September 3, 2024  
INVENTOR(S) : Manoj K. Jain et al.

Page 1 of 1

It is certified that error appears in the above-identified patent and that said Letters Patent is hereby corrected as shown below:

In the Claims

In Column 31, Line 53, Claim 10, delete "response request." and insert -- request. --, therefor.

In Column 32, Line 4, Claim 11, delete "determine" and insert -- determine, --, therefor.

In Column 32, Line 65, Claim 16, delete "determine" and insert -- determine, --, therefor.

Signed and Sealed this  
Tenth Day of December, 2024

Katherine Kelly Vidal  
*Director of the United States Patent and Trademark Office*